(12) United States Patent
Scheuring et al.

(10) Patent No.: US 10,022,293 B2
(45) Date of Patent: Jul. 17, 2018

(54) DEVICES AND METHODS FOR SEXUAL WELLNESS

(71) Applicant: STANDARD INNOVATION SARL, Luxembourg (LU)

(72) Inventors: Adam Scheuring, Oslo (NO); Anders Guldahl, Oslo (NO); Line Iren Andersen, Oslo (NO); Karianne Rønning Ellekrans, Hägersten (SE)

(73) Assignee: STANDARD INNOVATION CORPORATION, Ottawa (CA)

( * ) Notice: Subject to any disclaimer, the term of this patent is extended or adjusted under 35 U.S.C. 154(b) by 0 days.

(21) Appl. No.: 14/853,132

(22) Filed: Sep. 14, 2015

(65) Prior Publication Data

US 2016/0074276 A1    Mar. 17, 2016

Related U.S. Application Data

(60) Provisional application No. 62/050,115, filed on Sep. 13, 2014.

(51) Int. Cl.
*A61B 5/02* (2006.01)
*A61H 19/00* (2006.01)
(Continued)

(52) U.S. Cl.
CPC .............. *A61H 19/44* (2013.01); *A61B 5/01* (2013.01); *A61B 5/02416* (2013.01);
(Continued)

(58) Field of Classification Search
CPC ...... A61H 19/44; A61H 19/34; A61H 9/0078; A61H 9/0071; A61H 19/40;
(Continued)

(56) References Cited

U.S. PATENT DOCUMENTS

| 4,050,449 | A | 9/1977 | Castellana et al. |
| 4,574,791 | A | 3/1986 | Mitchener |

(Continued)

FOREIGN PATENT DOCUMENTS

| CA | 2236105 A1 | 11/1996 |
| CA | 2391521 A1 | 5/2001 |

(Continued)

OTHER PUBLICATIONS

European Patent Office, "Partial European Search Report dated Feb. 4, 2016 in corresponding European Application No. 15184993.2", dated Feb. 4, 2016, pp. 1-8, Germany.

(Continued)

*Primary Examiner* — Rex R Holmes
(74) *Attorney, Agent, or Firm* — The Law Office of Michael E. Kondoudis

(57) ABSTRACT

Some adult devices are ostensibly marketed to improve female sexual experience female by offering exercises to address relaxed vaginal muscles from birth, age, surgery etc. and for reducing incontinence. However, such devices suffer from variable placement by the user both in terms of orientation and penetrative depth such that the "results" are not reproducible and captured data used to provide feedback to the user and/or providing visual/audible prompts is flawed. Accordingly, it would be beneficial to provide a device with reproducible placement and data for enhancing the usability/benefit of the exercise regimen. It would be further beneficial for the device to either provide this exercise regime as part of a wider assessment of sexual wellness or as part of a sexual stimulation activity thereby reducing the focus on "exercise" to derive the benefits of improved pelvic muscle control.

18 Claims, 15 Drawing Sheets

(51) Int. Cl.
- *A61H 9/00* (2006.01)
- *A61H 21/00* (2006.01)
- *A61H 23/02* (2006.01)
- *A61B 5/01* (2006.01)
- *A61B 5/024* (2006.01)
- *A61B 5/00* (2006.01)
- *A61B 7/02* (2006.01)
- *A61N 1/36* (2006.01)
- *A61B 5/0205* (2006.01)
- *A61B 5/22* (2006.01)

(52) U.S. Cl.
CPC ............ *A61B 5/486* (2013.01); *A61B 5/6887* (2013.01); *A61B 7/023* (2013.01); *A61H 9/0071* (2013.01); *A61H 9/0078* (2013.01); *A61H 19/34* (2013.01); *A61H 19/40* (2013.01); *A61H 21/00* (2013.01); *A61H 23/02* (2013.01); *A61H 23/0263* (2013.01); *A61B 5/02055* (2013.01); *A61B 5/227* (2013.01); *A61B 5/4337* (2013.01); *A61B 2562/0247* (2013.01); *A61H 2201/0103* (2013.01); *A61H 2201/501* (2013.01); *A61H 2201/5007* (2013.01); *A61H 2201/5012* (2013.01); *A61H 2201/5015* (2013.01); *A61H 2201/5048* (2013.01); *A61H 2201/5071* (2013.01); *A61H 2201/5082* (2013.01); *A61H 2201/5084* (2013.01); *A61H 2201/5092* (2013.01); *A61H 2201/5097* (2013.01); *A61H 2230/06* (2013.01); *A61H 2230/065* (2013.01); *A61H 2230/08* (2013.01); *A61H 2230/085* (2013.01); *A61H 2230/207* (2013.01); *A61H 2230/208* (2013.01); *A61H 2230/25* (2013.01); *A61H 2230/255* (2013.01); *A61H 2230/30* (2013.01); *A61H 2230/305* (2013.01); *A61H 2230/60* (2013.01); *A61H 2230/605* (2013.01); *A61N 1/36007* (2013.01)

(58) Field of Classification Search
CPC .... A61H 23/0263; A61H 21/00; A61H 23/02; A61B 5/02416; A61B 7/023; A61B 5/486; A61B 5/6887; A61B 5/01; A61B 5/4337; A61B 5/02055
See application file for complete search history.

(56) References Cited

U.S. PATENT DOCUMENTS

| | | | |
|---|---|---|---|
| 4,909,263 A * | 3/1990 | Norris | A61N 1/0524 600/551 |
| 5,733,230 A | 3/1998 | Sawchuck et al. | |
| D398,402 S | 9/1998 | Kirk et al. | |
| 5,853,376 A | 12/1998 | Harris | |
| 5,993,377 A | 11/1999 | Hartwig | |
| 6,063,045 A | 5/2000 | Wax et al. | |
| 6,102,876 A | 8/2000 | Winger | |
| 6,165,108 A | 12/2000 | Ralston | |
| 6,217,529 B1 | 4/2001 | Wax et al. | |
| 6,370,912 B1 | 4/2002 | Sutton | |
| 6,394,939 B1 | 5/2002 | Stein | |
| 6,406,411 B1 | 6/2002 | Guagliano et al. | |
| 6,432,037 B1 | 8/2002 | Eini et al. | |
| 6,530,879 B1 | 3/2003 | Adamkiewicz | |
| 6,562,018 B1 | 5/2003 | Russell | |
| 6,672,996 B2 | 1/2004 | Ross et al. | |
| 6,723,031 B1 | 4/2004 | Wild | |
| 6,905,471 B2 | 6/2005 | Leivseth et al. | |
| RE38,924 E | 12/2005 | Reynard et al. | |
| 7,001,317 B2 | 2/2006 | Marcotte | |
| 7,056,278 B2 | 6/2006 | Adamkiewicz | |
| D553,253 S | 10/2007 | Gayne | |
| 7,351,195 B2 | 4/2008 | Farrell | |
| 7,473,214 B2 | 1/2009 | Schuurmans Stekhoven et al. | |
| 7,628,744 B2 | 12/2009 | Hoffman et al. | |
| 7,645,220 B2 | 1/2010 | Hoffman et al. | |
| 7,955,241 B2 | 6/2011 | Hoffman et al. | |
| 7,957,794 B2 | 6/2011 | Hochman et al. | |
| 7,998,056 B2 | 8/2011 | Sifter et al. | |
| D649,654 S | 11/2011 | Levine | |
| 8,308,667 B2 | 11/2012 | Lee | |
| 8,360,956 B2 | 1/2013 | Squicciarini | |
| D677,385 S | 3/2013 | Takashima | |
| D687,959 S | 8/2013 | Reichmann et al. | |
| 8,512,226 B2 | 8/2013 | Mark | |
| D703,342 S | 4/2014 | Faussett | |
| D705,941 S | 5/2014 | Hahr et al. | |
| D706,442 S | 6/2014 | Hahr et al. | |
| D712,029 S | 8/2014 | Tai | |
| D712,030 S | 8/2014 | Tai | |
| 8,870,724 B2 | 10/2014 | Armitage et al. | |
| 2003/0040688 A1 | 2/2003 | Bauer | |
| 2005/0130818 A1 | 6/2005 | Karol | |
| 2005/0148447 A1 | 7/2005 | Nady | |
| 2006/0036188 A1 | 2/2006 | Hoffman et al. | |
| 2009/0275796 A1 | 11/2009 | Gil | |
| 2009/0281397 A1 | 11/2009 | Lavoisier | |
| 2010/0174137 A1 | 7/2010 | Shim | |
| 2010/0174214 A1 | 7/2010 | Baniel et al. | |
| 2010/0174218 A1 | 7/2010 | Shim | |
| 2011/0071446 A1 | 3/2011 | Citrin | |
| 2012/0053017 A1 | 3/2012 | Kushnir | |
| 2013/0060177 A1 | 3/2013 | Kunnecke | |
| 2013/0085047 A1 | 4/2013 | Bloch | |
| 2013/0116503 A1 | 5/2013 | Mertens et al. | |
| 2013/0130871 A1 | 5/2013 | McCoy et al. | |
| 2013/0172793 A1 | 7/2013 | Takashima | |
| 2013/0331745 A1 | 12/2013 | Sedic | |
| 2014/0088471 A1 | 3/2014 | Leivseth | |
| 2014/0155225 A1 | 6/2014 | Sedic | |
| 2014/0163437 A1 | 6/2014 | Mack et al. | |
| 2014/0200646 A1 | 7/2014 | Boyd et al. | |
| 2014/0236151 A1 | 8/2014 | Lee | |
| 2014/0243590 A1 | 8/2014 | Fang et al. | |
| 2015/0196802 A1 | 7/2015 | Siegel | |
| 2015/0273270 A1 | 10/2015 | Brinkhaus et al. | |
| 2015/0328082 A1 * | 11/2015 | Jiang | A61H 19/00 600/38 |
| 2016/0000642 A1 * | 1/2016 | Zipper | A61H 19/44 600/38 |
| 2016/0008664 A1 | 1/2016 | Siegel | |
| 2016/0279469 A1 | 9/2016 | Rose | |

FOREIGN PATENT DOCUMENTS

| | | | |
|---|---|---|---|
| CA | 2452143 A1 | 5/2005 | |
| CA | 2312401 C | 1/2007 | |
| CA | 2671512 A1 | 5/2008 | |
| CA | 2673567 C | 6/2008 | |
| CA | 2311246 C | 3/2009 | |
| EP | 1032457 B1 | 8/2002 | |
| EP | 1034016 B1 | 7/2007 | |
| EP | 1231859 B1 | 10/2007 | |
| EP | 1487335 B1 | 10/2010 | |
| EP | 001374938-0005 | 9/2013 | |
| EP | 001374938-0006 | 9/2013 | |
| EP | 001374938-0007 | 9/2013 | |
| EP | 001374938-0008 | 9/2013 | |
| EP | 001374938-0009 | 9/2013 | |
| EP | 001374938-00010 | 9/2013 | |
| EP | 002345256-001 | 11/2013 | |
| EP | 2708187 A1 | 3/2014 | |
| MX | 039992 | 11/2013 | |
| WO | 2000041772 A1 | 7/2000 | |
| WO | 2004075969 A1 | 9/2004 | |
| WO | 2005049151 A1 | 6/2005 | |
| WO | 2007056559 A1 | 5/2007 | |
| WO | 2007059988 A1 | 5/2007 | |
| WO | 2007059989 A1 | 5/2007 | |
| WO | 2008063085 A1 | 5/2008 | |
| WO | 2008077144 A1 | 6/2008 | |

(56) References Cited

FOREIGN PATENT DOCUMENTS

| WO | 2010079931 A1 | 7/2010 |
|---|---|---|
| WO | 2011/159906 A2 | 12/2011 |
| WO | 2012016005 A1 | 2/2012 |
| WO | 2012079127 A1 | 6/2012 |
| WO | 2013067367 A1 | 5/2013 |
| WO | 2013131839 A1 | 9/2013 |
| WO | 2013/147992 | 10/2013 |
| WO | 2014015901 A1 | 1/2014 |
| WO | 2014013118 A9 | 3/2014 |
| WO | 2014043263 A1 | 3/2014 |
| WO | 2014127526 A1 | 8/2014 |
| WO | 2015103629 A1 | 7/2015 |
| WO | 2015106199 A1 | 7/2015 |
| WO | 2016101070 A1 | 6/2016 |
| WO | 2016119002 A1 | 8/2016 |
| WO | 2016154421 A1 | 9/2016 |

OTHER PUBLICATIONS

European Patent Office, "International Search Report dated May 4, 2016 in corresponding International Application No. PCT/IB2015/002142", dated May 4, 2016, Netherlands.

European Patent Office, "Extended European Search Report dated Jun. 6, 2016 in corresponding European Application No. 15184993.2", dated Jun. 6, 2016, Germany.

International Bureau, "International Preliminary Report on Patentability dated Mar. 14, 2017 in corresponding International Application No. PCT/IB2015/002142", dated Mar. 14, 2017, Switzerland.

* cited by examiner

Section X-X

Section Y-Y

Section Z-Z

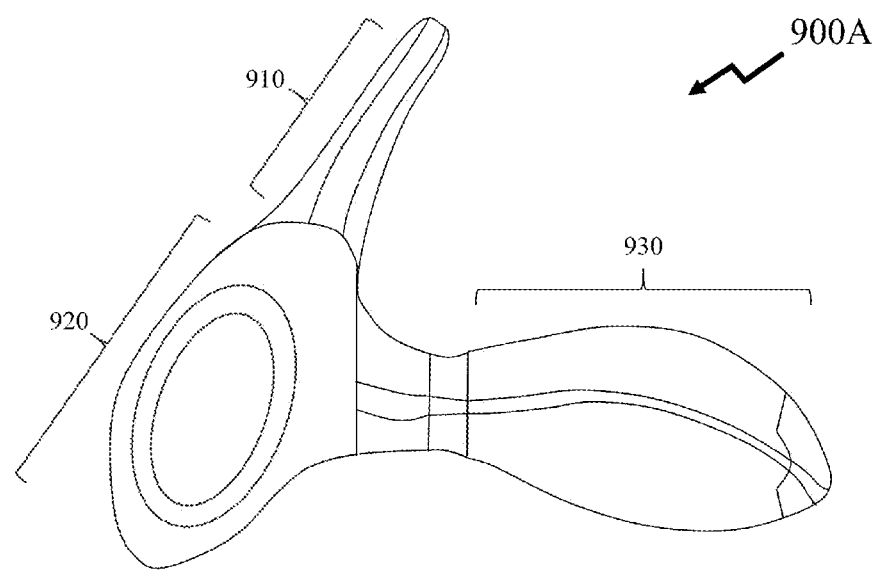
Figure 9
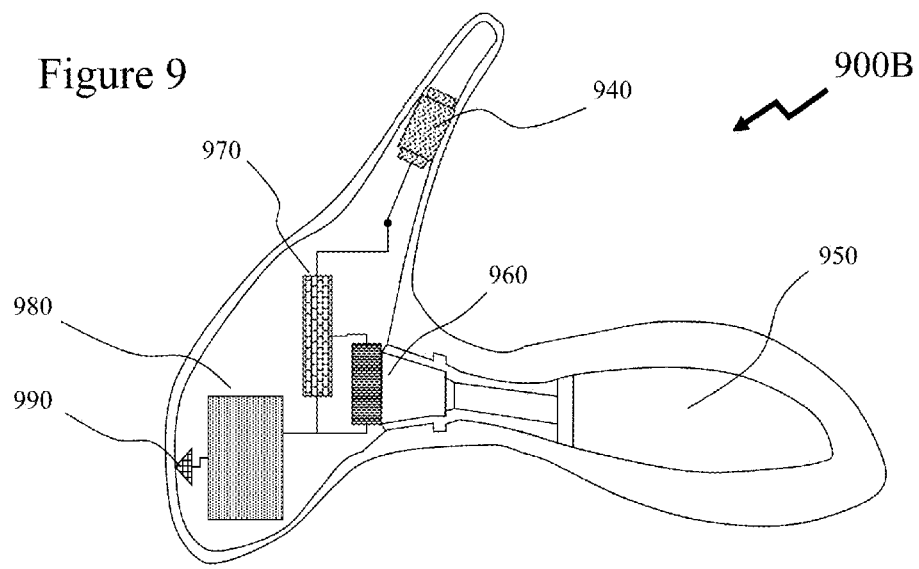

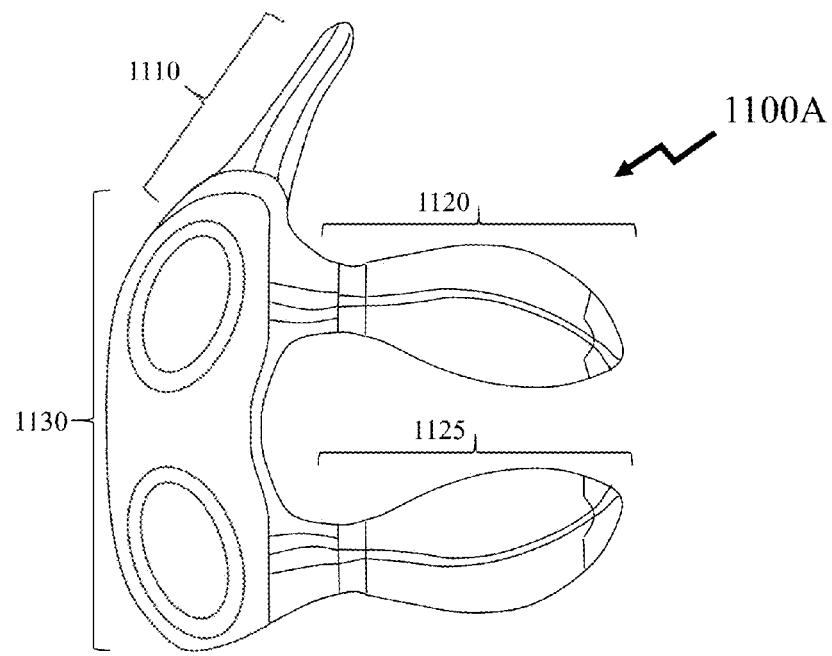
Figure 11A
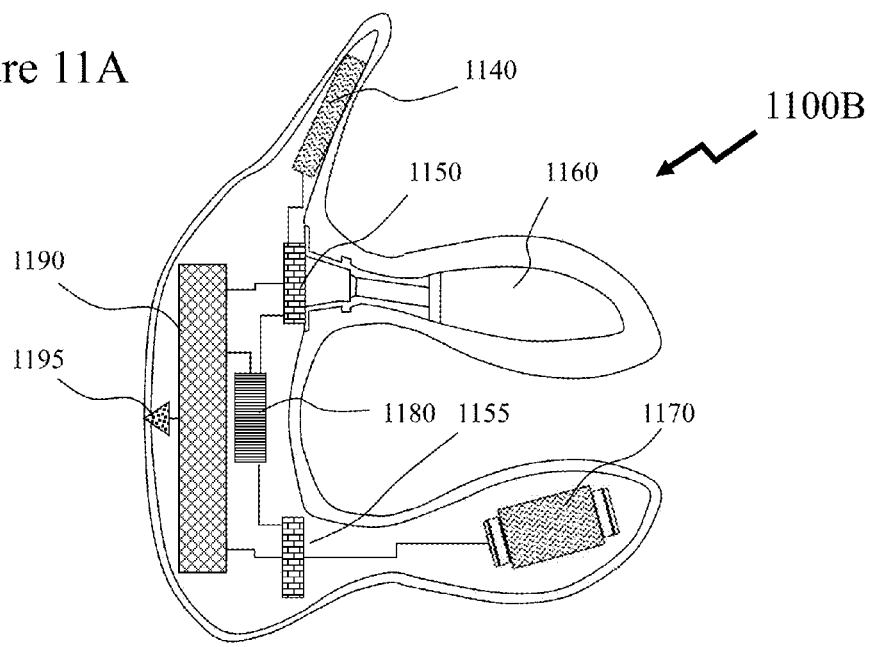

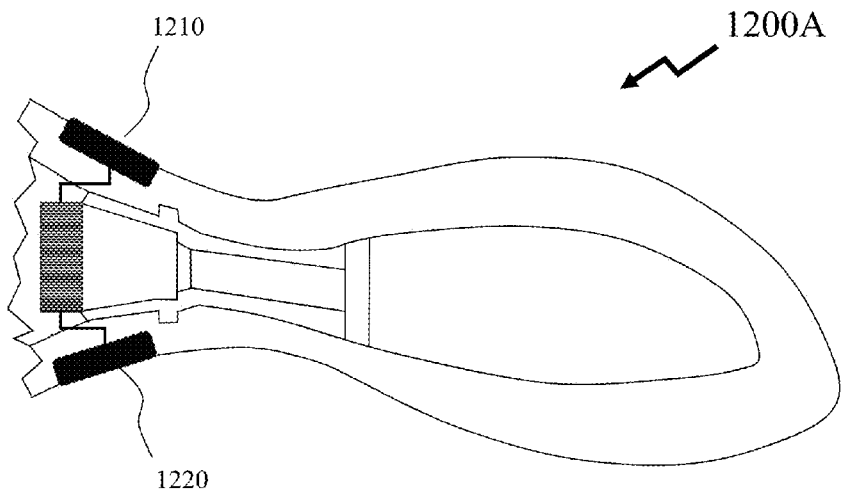
Figure 12
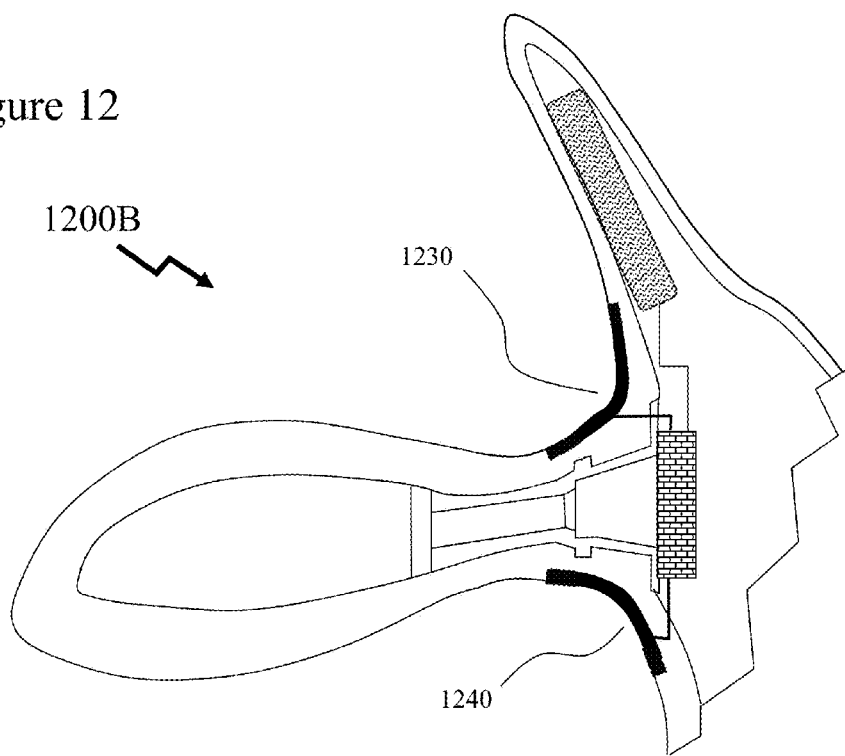

DEVICES AND METHODS FOR SEXUAL WELLNESS

CROSS-REFERENCE TO RELATED APPLICATIONS

This patent application claims the benefit of U.S. Provisional Patent Application 62/050,115 filed Sep. 13, 2014 entitled "Device and Method of Pelvic Floor Muscle Exercise", the entire contents of which are included by reference.

FIELD OF THE INVENTION

This invention relates to adult devices and more particularly to the provisioning of pelvic and sphincter muscle monitoring within devices assessing sexual wellness and/or providing sexual stimulation.

BACKGROUND OF THE INVENTION

A sex toy or adult device is an object or device that is primarily used to facilitate human sexual pleasure which are typically designed to resemble human genitals and may be mechanized and non-mechanized. Mechanized adult devices typically vibrate, although there are examples that rotate, thrust, and even circulate small beads within an elastomeric shell. Non-mechanized adult devices are made from a solid mass of rigid or semi-rigid material in a variety of shapes. Accordingly, today, a wide range of adult devices are offered commercially to users with the majority of them falling into several broad categories including clitoral, (G-spot), dildo, rabbit (generally comprising two vibrators, one phallus-like shaped intended for insertion and a second smaller clitoral stimulator), egg (small smooth vibrators for external or internal stimulation although now offered in a range of shapes), anal, penis ring, bullet (small cylindrical vibrators), c-shaped (for generally hands free use by insertion into the vagina with one or two vibrators for clitoral and/or g-spot stimulation including variants for use during penile penetration) and Butterfly (generally a vibrator with straps). Further, for men there are adult devices with a range of vibrations and movements associated with the penis.

In addition there are devices such as Kegel balls or Ben-Wa balls which are ostensibly marketed to improve the sexual experience for the female user by offering vaginal muscle exercises to address relaxed vaginal muscles from birth, age, surgery etc. and also to reduce female incontinence. However, these generally include vibrating elements and hence are also categorized under adult devices rather than medical devices. However, such devices are generally subject to variable placement by the user both in terms of orientation and penetrative depth such that the "results" are not reproducible such that the data captured by the software application providing feedback to the user and/or providing visual/audible prompts is flawed.

Accordingly, it would be beneficial to provide users with a device that provide reproducible placement and accordingly reproducible data for enhancing the usability/benefit of the user following an exercise regimen. It would be further beneficial for the device to either provide the exercise regime as part of a wider assessment of sexual wellness for the user or provide the exercise regime as part of a sexual stimulation activity so that the user does not always have to perform an "exercise" to derive the benefits of improved pelvic muscle control.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations within the prior art relating to adult devices and more particularly to the provisioning of pelvic muscle monitoring within devices assessing sexual wellness and/or providing sexual stimulation.

In accordance with an embodiment of the invention there is provided a sexual wellness device comprising:
a pillow formed from a flexible material defining an inner volume and having an opening at an end; and
a socket formed from an inflexible material having in a first predetermined location a fitting onto which the open end of the pillow mounts, a pressure sensor fluidically coupled to the fitting, a controller electrically coupled to the pressure sensor, and a battery electrically connected to at least the controller.

In accordance with an embodiment of the invention there is provided a method of adjusting sexual wellness for a user comprising:
providing a pillow formed from a flexible material defining an inner volume and having an opening at an end;
providing a socket formed from an inflexible material having in a first predetermined location a fitting onto which the open end of the pillow mounts, a pressure sensor fluidically coupled to the fitting, a controller electrically coupled to the pressure sensor, and a battery electrically connected to at least the controller; and
monitoring an action of the user with respect to the pillow resulting in a pressure fluctuation and providing the user with feedback as to their performance.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 9 depicts a side view and a cross-sectional side view of an adult device according to an embodiment of the invention with additional clitoral stimulator;

FIG. 11A depicts a side view and a cross-sectional side view of an adult device according to an embodiment of the invention with vaginal and anal elements together with a clitoral stimulator;

FIG. 12 depicts portions of an adult device according to an embodiment of the invention depicting additional labial thermistors for arousal monitoring;

DETAILED DESCRIPTION

Figure 1:
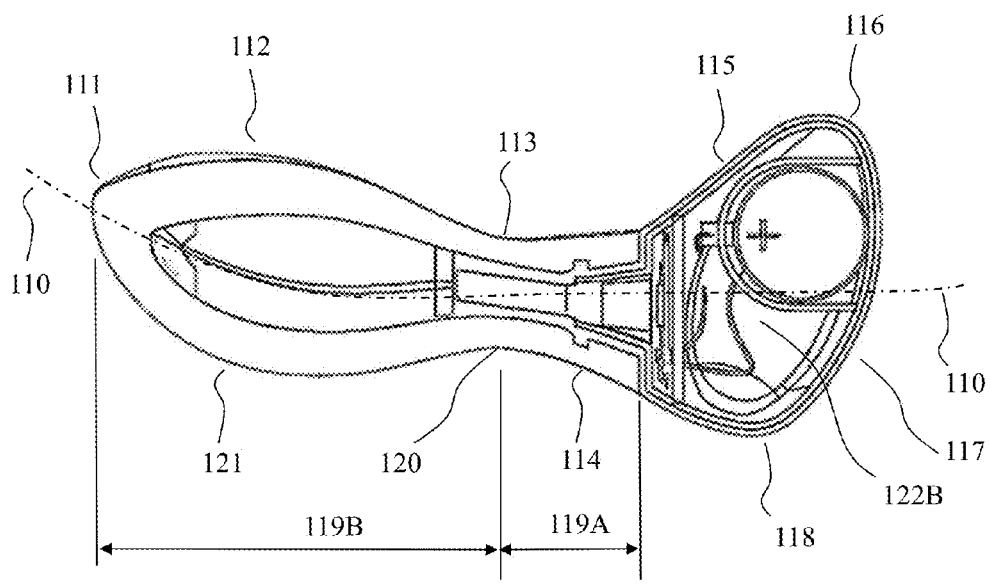
FIG. 1 depicts a cross section of an adult device according to an embodiment of the invention with three dimensional (3D) surface curvature highlighted.

The present invention is directed to adult devices and more particularly to the provisioning of pelvic muscle monitoring within devices assessing sexual wellness and/or providing sexual stimulation.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included. Similarly, "option", "mode", alternative", "feature", "an embodiment" are when used in the context of describing this invention, referring specifically to various embodiments of this invention. All descriptions herein are non-limiting, as one trained in the art will appreciate, and that alternate embodiments of the invention other that those described are possible and/or feasible.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users. Reference to terms "including", "comprising", "consisting" and grammatical variants thereof do not preclude the addition of one or more components, features, steps, integers or groups thereof and that the terms are not to be construed as specifying components, features, steps or integers. Likewise the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

Any reference within this specification in respect of physical axes is such that the vagina is assumed to run from the distal end of the superior-inferior human axis proximal towards the superior end of the axis. The entrance to the vagina is approximately in the transverse plane. Accordingly, the "Y" axis, where referenced and/or depicted, is along the superior-inferior axis, with positive towards the superior. The "X" axis, where referenced and/or depicted, is in the anteroposterior axis, with positive towards posterior.

A "portable electronic device" (PED) as used herein and throughout this disclosure, refers to a wireless device used for communications and other applications that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, a wearable device and an electronic reader.

A "fixed electronic device" (FED) as used herein and throughout this disclosure, refers to a wireless and/or wired device used for communications and other applications that requires connection to a fixed interface to obtain power. This includes, but is not limited to, a laptop computer, a personal computer, a computer server, a kiosk, a gaming console, a digital set-top box, an analog set-top box, an Internet enabled appliance, an Internet enabled television, and a multimedia player.

A "server" as used herein, and throughout this disclosure, refers to one or more physical computers co-located and/or geographically distributed running one or more services as a host to users of other computers, PEDs, FEDs, etc. to serve the client needs of these other users. This includes, but is not limited to, a database server, file server, mail server, print server, web server, gaming server, or virtual environment server.

An "application" (commonly referred to as an "app") as used herein may refer to, but is not limited to, a "software application", an element of a "software suite", a computer program designed to allow an individual to perform an activity, a computer program designed to allow an electronic device to perform an activity, and a computer program designed to communicate with local and/or remote electronic devices. An application thus differs from an operating system (which runs a computer), a utility (which performs maintenance or general-purpose chores), and a programming tools (with which computer programs are created). Generally, within the following description with respect to embodiments of the invention an application is generally presented in respect of software permanently and/or temporarily installed upon a PED and/or FED.

A "user" as used herein may refer to, but is not limited to, an individual or group of individuals. This includes, but is not limited to, private individuals, employees of organizations and/or enterprises, members of community organizations, members of charity organizations, men and women. In its broadest sense the user may further include, but not be limited to, software systems, mechanical systems, robotic systems, android systems, etc. that may be characterised by an ability to exploit one or more embodiments of the invention. A user may be associated with biometric data which may be, but not limited to, monitored, acquired, stored, transmitted, processed and analysed either locally or remotely to the user. A user may also be associated through one or more accounts and/or profiles with one or more of a service provider, third party provider, enterprise, social network, social media etc. via a dashboard, web service, website, software plug-in, software application, and graphical user interface.

"User information" as used herein may refer to, but is not limited to, user behavior information and/or user profile information. It may also include a user's biometric information, an estimation of the user's biometric information, or a projection/prediction of a user's biometric information derived from current and/or historical biometric information.

A "wearable device" or "wearable sensor" relates to miniature electronic devices that are worn by the user including those under, within, with or on top of clothing and are part of a broader general class of wearable technology which includes "wearable computers" which in contrast are directed to general or special purpose information technologies and media development. Such wearable devices and/or wearable sensors may include, but not be limited to, smartphones, smart watches, e-textiles, smart shirts, activity trackers, smart glasses, environmental sensors, medical sensors, biological sensors, physiological sensors, chemical sensors, ambient environment sensors, position sensors, neurological sensors, drug delivery systems, medical testing and diagnosis devices, and motion sensors. The wearable devices and/or wearable sensors may include, but not be limited to, devices that can stimulate and/or measure parameters that are designed to fit on or near the perineum, anal area, vagina, clitoral area, and nipples.

"Biometric" information as used herein may refer to, but is not limited to, data relating to a user characterised by data relating to a subset of conditions including, but not limited to, their environment, medical condition, biological condition, physiological condition, chemical condition, ambient environment condition, position condition, neurological condition, drug condition, and one or more specific aspects of one or more of these said conditions. Accordingly, such biometric information may include, but not be limited, blood oxygenation, blood pressure, blood flow rate, heart rate, temperate, fluidic pH, viscosity, particulate content, solids content, altitude, vibration, motion, perspiration, EEG, ECG, energy level, etc. In addition biometric information may include data relating to physiological characteristics related to the shape and/or condition of the body wherein examples may include, but are not limited to, fingerprint, facial geometry, baldness, DNA, hand geometry, odour, and scent. Biometric information may also include data relating to behavioral characteristics, including but not limited to, typing rhythm, gait, and voice.

An "adult device", "sexual pleasure device", or "sex toy" as used herein, and throughout this disclosure, refers to a sexual pleasure device intended for use by an individual or user themselves or in conjunction with activities with another individual or user which can provide one or more functions including, but not limited to, those of a dildo and a vibrator. The adult device can be designed to have these functions in combination with design features that are intended to be penetrative or non-penetrative, provide vibratory and non-vibratory mechanical functions, or be passive. Such adult devices can be designed for use with one or more regions of the male and female bodies including but not limited to, the clitoris, the clitoral area (which is the area surrounding and including the clitoris), vagina, rectum, nipples, breasts, penis, testicles, prostate, and "G-spot." In one example a "male adult device" is an adult device configured to receive a user's penis within a cavity or recess. In another example, a "female adult device" is an adult device having at least a portion configured to be inserted in a user's vagina or rectum. It should be understood that the user of a female adult device can be a male or a female when it is used for insertion in a user's rectum. Such adult devices may employ one or more actuation mechanisms when providing vibratory and non-vibratory mechanical functions including, but not limited to, motors, motors with off-axis weights, linear motors, screw drives, fluidic pumps, fluidic actuators, and piezoelectric elements.

An "accessory" or "accessories" as used herein, and throughout this disclosure, refers to one or more objects that can be affixed to or otherwise appended to the body of a sexual pleasure device in order to enhance and/or adjust the sensation(s) provided. Such accessories can be passive, such as nubbies or a dildo, or active, such as a vibrator.

A "profile" as used herein, and throughout this disclosure, refers to a computer and/or microprocessor readable data file comprising data relating to settings and/or limits of an adult device. Such profiles may be established by a manufacturer of the adult device or established by an individual through a user interface to the adult device or a PED/FED in communication with the adult device.

A "vibrator" as used herein, and throughout this disclosure, refers to an electronic sexual pleasure device intended for use by an individual or user themselves or in conjunction with activities with another individual or user wherein the vibrator provides a vibratory mechanical function for stimulating nerves or triggering physical sensations.

A "dildo" as used herein, and throughout this disclosure, refers to a sexual pleasure device intended for use by an individual or user themselves or in conjunction with activities with another individual or user wherein the dildo provides non-vibratory mechanical function for stimulating nerves or triggering physical sensations.

A "nubby" or "nubbies" as used herein, and throughout this disclosure, refers to a projection or projections upon the surface of a sexual pleasure device intended to provide additional physical interaction. A nubby can be permanently part of the sexual pleasure device or it can be replaceable or interchangeable to provide additional variation to the sexual pleasure device.

An "accessory" or "accessories" as used herein, and throughout this disclosure, refers to one or more objects that can be affixed to or otherwise appended to the body of a sexual pleasure device in order to enhance and/or adjust the sensation(s) provided. Such accessories can be passive, such as nubbies or a dildo, or active, such as a vibrator.

A "scaffold" or "scaffolds" as used herein, and throughout this disclosure, refers to a structure that is used to hold up, interface with, or support another material or element(s). This includes, but is not limited to, such two-dimensional (2D) structures such as substrates and films, three-dimensional (3D) structures such as geometrical objects, non-geometrical objects, combinations of geometrical and non-geometrical objects, naturally occurring structural configurations, and manmade structural configurations. A scaffold may be solid, hollow, and porous or a combination thereof. A scaffold may contain recesses, pores, openings, holes, vias, and channels or a combination thereof. A scaffold may be smooth, textured, have predetermined surface profiles and/or features. A scaffold may be intended to support one or more other materials, one or more films, a multilayer film, one type of particle, multiple types of particles etc. A scaffold may include, but not be limited to, a spine of a device and/or a framework, for example, which also supports a shell and/or a casing.

A "shell" as used herein, and throughout this disclosure, refers to a structure that is used to contain and/or surround at least partially and/or fully a number of elements within adult devices according to embodiments of the invention. A shell may include, but not limited to, a part or parts that are mounted to a scaffold or scaffolds that support elements within a device according to an embodiment of the invention.

A "casing" as used herein, and throughout this disclosure, refers to a structure surrounding a scaffold and/or shell. This includes structures typically formed from an elastomer and/or silicone to provide a desired combination of physical tactile surface properties to the device it forms part of and other properties including, but not limited to, hermeticity, liquid ingress barrier, solid particulate ingress barrier, surface sheen, and colour. A casing may include, but not limited to, a part or parts that are mounted to a scaffold or scaffolds and/or a casing or casings forming part of a device according to an embodiment of the invention.

A "pillow" (also called a "sleeve") as used herein, and throughout this disclosure, refers to a flexible, compressible portion of an adult device designed for insertion into an orifice of a user, for example the vagina or anus. This may be a region of the adult device that is filled with a fluid, either liquid or gas, at atmospheric pressure, above atmospheric pressure or below atmospheric pressure. A pillow may be totally inserted or only a portion of the pillow may be inserted. A pillow may be shaped to fit the orifice for which it is intended to be inserted, e.g. the vagina or anus, but it would be evident that the pillow may also be inserted into an orifice it is not designed for or that the pillow may be generically shaped for insertion into any orifice.

A "polyester" as used herein, and throughout this disclosure, refers to a category of polymers that contain the ester functional group in their main chain. This includes, but is not limited to polyesters which are naturally occurring chemicals as well as synthetics through step-growth polymerization, for example. Polyesters may be biodegradable or not. Polyesters may be a thermoplastic or thermoset or resins cured by hardeners. Polyesters may be aliphatic, semi-aromatic or aromatic. Polyesters may include, but not be limited to, those exploiting polyglycolide, polylactic acid (PLA), polycaprolactone (PCL), polyhydroxyalkanoate (PHA), polyhydroxybutyrate (PHB), polyethylene adipate (PEA), polybutylene succinate (PBS), polyethylene terephthalate (PET), polybutylene terephthalate (PBT), polytrimethylene terephthalate (PTT), and polyethylene naphthalate (PEN).

A "thermoplastic" or "thermosoftening plastic" as used herein and throughout this disclosure, refers to a category of polymers that become pliable or moldable above a specific temperature and solidify upon cooling. Thermoplastics may include, but not be limited, polycarbonate (PC), polyether sulfone (PES), polyether ether ketone (PEEK), polyethylene (PE), polypropylene (PP), poly vinyl chloride (PVC), polytetrafluoroethylene (PTFE), polyimide (PI), polyphenylsulfone (PPSU), polychlorotrifluoroethene (PCTFE or PTFCE), fluorinated ethylene propylene (FEP), and perfluoroalkoxy alkane (PFA).

A "metal" as used herein, and throughout this disclosure, refers to a material that has good electrical and thermal conductivity. Such materials may be malleable and/or fusible and/or ductile. Metals may include, but not be limited to, aluminum, nickel, copper, cobalt, chromium, silver, gold, platinum, iron, zinc, titanium, and alloys thereof such as bronze, stainless steel, stainless stainless steel, brass, and phosphor bronze.

A "silicone" as used herein, and throughout this disclosure, refers to a polymer that includes any inert, synthetic compound made up of repeating units of siloxane.

An "elastomeric" material or "elastomer" as used herein, and throughout this disclosure, refers to a material, generally a polymer, with viscoelasticity. Elastomers may include, but not be limited to, unsaturated rubbers such as polyisoprene, butyl rubber, ethylene propylene rubber, silicone rubber, fluorosilicone rubber, fluoroelastomers, perfluoroelastomers, and thermoplastic elastomers.

The terms "woman" or "female" as used herein, and throughout this disclosure, refers to a human having a clitoris or clitoral region and, optionally, a vagina and/or an anus. The terms "woman" and "female" are used interchangeably herein. A female may be a user, an individual, another user, and/or another individual within contexts of the specification.

The terms "man" or "male" as used herein, and throughout this disclosure, refers to a human having a penis and, optionally, testes and/or an anus. The terms "man" and "male" are used interchangeably herein. A male may be a user, an individual, another user, and/or another individual within contexts of the specification.

The term "flexible," as used herein, refers to the ability of a body that is capable of being bent or flexed. Something that is flexible can be, for example, resilient or malleable. The term "resilient," as used herein, refers to the ability of a body that has been subjected to an external force to recover, or substantially recover, its original size and/or shape, following deformation. The term "malleable," as used herein, refers to the ability of a body that has been subjected to an external force to deform and maintain, or substantially maintain, the deformed size and/or shape. The term "flexible," as used herein, refers to the ability of a body that has been subjected to an external force to return to its original size and/or shape once the external force has been removed or reduced to below a particular level.

As used herein, the terms "sex", "intercourse", "sexual intercourse" are intended to have a meaning referring to an act or action between two users wherein part of the act or action relates to the stimulation of one user's or both user's clitoris and/or clitoral region. Such acts or actions may or may not involve the concurrent penetration of a user's vagina, anus, or mouth and may be male-female, female-female, and solitary female based acts or actions.

Referring to FIGS. 1-4 and 8 respectively there are depicted an embodiment of the invention comprising the following components:

a flexible sleeve, or pillow, which is inserted into the vagina;
a socket; and
an electronics module.

Some embodiments of the invention may include software and/or firmware in conjunction with the hardware to provide the adult device systems, applications, and platforms (ADSAPs) as described and discussed within this specification.

ADult DEVices (ADDEVs) according to embodiments of the invention exploit a sleeve or pillow is hollow with an air chamber or chambers inside. When the pillow is squeezed, its volume reduces causing a pressure increase. The pillow is attached to the socket via an airtight joint or coupling wherein an airway connects the air in the pillow to air in the socket. Within the socket is a pressure sensor. The socket is made from a low flexibility material so that its volume changes minimally with pressure and accordingly by virtue of being less flexible it changes volume with pressure less than the pillow such that the pillow volume changes dominate in the pressure variations coupled through the airway to the pressure sensor or pressure sensors. For example, the pillow may be formed from a medical grade silicone whilst the socket may be plastic formed, for example, from acrylonitrile butadiene styrene (ABS), low density polyurethane (LDPE), polyvinyl chloride (PVC), polypropylene, polyamides, and polycarbonate.

The airway connects the chamber in the interior of the socket and may have a single compartment or more than one compartment, with respect to airflow as well as in respect to multiple chambers within the pillow. The use of the airway is novel as it is possible to restrict the airflow from the pillow chamber to the socket and back in a manner that a time constant for two-way airflow is created. This time constant represents an improvement over prior art and, the airway, in some embodiments, behaves as a constricting airway causing the return air from the socket to the pillow to be slowed when the muscles relax, causing a slower rate of return to the original size of the pillow. Advantageously, the pillow-socket arrangement permits complete compression of the pillow during muscle contraction. That is, compared to prior art, the volume reduction of the pillow is not blocked by an incompressible element in the pillow.

Further, as will become evident in the description below and outlined above the geometry of the pillow has been established in order to provide several key benefits. Considering, an adult device with a pillow for vaginal insertion these benefits include:

superior positioning within the vagina;
increased comfort for the user;
improved placement consistency within the vagina, which permits more accurate measurement of muscle contractions and more accurate progress measurement;
superior sensitivity to the upper portion of the muscles; and
the asymmetric shape of the adult device provides a superior fit to the muscles as it more accurately matches natural muscle shape.

In addition to the novel shape of the pillow the inventors have established a novel shape of the handle as the adult device may be employed not only by a user personally but also by medical personnel within a clinical environment, doctors surgery etc. Accordingly, the handle is designed for benefits including:

providing improved comfort to the patient during insertion and removal;
provides improved comfort to the user when using the device;
improving placement control of the adult device for the user;
providing improved placement control for a doctor or therapist, as compared to prior art.

The handle should be large enough for comfort and control, yet light enough to avoid incorrect or inconsistent measurements. The novel shape of the handle provides an improvement over prior art.

Referring to FIG. 1 there is depicted a cross-section of an ADult DEVice (ADDEV) according to an embodiment of the invention. The shape of the ADDEV, in numerous embodiments, provides novel improvements over the prior art in terms of fit, convenience, and function. Depicted is a curved line representing device plane 110 which runs along the axis of the device and is, approximately, in the sagittal plane of the user's body when the device is in use, approximately aligned to the superior-inferior axis of the user within their vagina. Importantly, device plane 110 is not represented by a straight line, or a simple radius curve, as employed within devices in the prior art. Within the embodiment depicted, device plane 110 has a smaller radius near the superior tip 111 of the device, and a larger radius near the inferior end, through the handle 117. Tip 111 shows the superior top of the device wherein the radius of the tip 111, which is much smaller than the radii of the upper portion 112 and lower portion 121 for the body of the pillow. The radius of the tip 111 may be less than half, less than a quarter, less than an eighth, or less than a tenth the radius of either the surface of the upper portion 112 or lower portion 121. The radius of the upper portion 112 defines the upper curve of the pillow which, in this embodiment of the invention, faces the anterior surface of vagina, in use. Within this embodiment of the invention the radius of the upper portion 112 is a smooth joining curve with the curves of the top 111 and upper neck portion 113, and may not be a uniform radius along its length, as shown. The average radius for upper surface 112 may be in the range of 25 mm to 500 mm (1" to 20"), or in the range of 50 mm to 250 mm (2" to 10"), or in the range of 75 mm to 175 mm (3" to 7"). The concave radius of the upper neck portion 113 defines the change from the primary pillow radius defined by the upper portion 112 to create the neck of the pillow, at or near the minimum diameter of the device. This radius may be in the range of 0 mm to 1000 mm (0" to 40"), or in the range of 12.5 mm to 500 mm (½" to 20"). Optionally, another portion of the neck at or adjacent to the radius of upper neck portion 113 may be straight.

Still referring to FIG. 1, upper surface 115 defines the upper surface of the handle, which may be facing the user's pubic bone, when the device is in use, for the embodiment of the invention for vaginal insertion. This surface may be straight, or have a concave or convex radius larger than 12.5 mm (½") or larger than 50 mm (2"). This surface may in embodiments of the invention be a concave portion of a sphere or ellipsoid, surface 61 in FIG. 4, where the recess created by the shape provides a place for the thumb of the user when inserting or removing the device. The radii of the portion of the sphere are larger than 1,500 m (60"), or larger than 500 mm (20"), or larger than 250 mm (10"), or larger than 125 mm (5"), or in the range of 12.5 mm to 250 mm (½" to 10"), or in the range of 25 mm to 125 mm (1" to 5"). The recess in this region, surface 61, may have two separate radii as in an ellipsoid.

Continuing with FIG. 1, transition surface 116 is a curve at the end of the handle 117. The radius for this curve may be in the range of 12.5 mm to 250 mm (½" to 10"). The rear surface of the handle 117 represents the region furthest from the user and may have a radius for this surface is in the range of 25 mm to infinity (1" to infinity), or in the range of 50 mm to 1,500 mm (2" to 60"), This surface may be concave or convex and transitions at the lower end to bottom 118 of the handle 117, which connects the bottom 118 of the handle 117 to the lower portion 114 of the neck of the ADDEV. The radius for this curve may be in the range of 12.5 mm to 500 mm (½" to 20"). Lower portion 114 is the lower, or posterior neck portion of the device where it mates with the socket. This portion may be straight, or have a concave radius in the range of 25 mm to infinity (1" to infinity). First and second measurement 119A and 119B depict the distance from the minimum diameter of the device at its neck to the junction between the pillow and the socket and the distance from the tip 111 to the junction between the pillow and the socket. The range for this distance can be 0 mm to 150 mm (0" to 6"), or in the range of 12.5 mm to 75 mm (½" to 3").

The concave surface 120 defines the posterior neck, or minimum diameter of the device, wherein this concave surface 120 may have the same range as upper neck portion 113, although it may be "smoother" with a larger radius than upper neck portion 113. Lower portion 121 is the posterior main curve for the pillow and the average radius for this curve may be in the same range as the curve for upper portion 112, although it may be longer due to the asymmetric shape as defined by device plane 110.

Referring further to FIG. 1, embodiments of the invention may be defined by none, one or more of the following relationships:
  tip radius 111 is smaller than the radii of upper portion 112 and lower portion 121;
  lower portion 121 has larger average radius than upper portion 112;
  transition surface 116 and bottom 118 have smaller radii than the transitionary surface joining them at the rear of the handle 117; and
  transition surface 116 and bottom 118 have smaller radii than upper surface 115 and lower portion 114.

Continuing further with FIG. 1, the angle of upper surface 15 with respect to the device plane 110, may be within the range 0° to 90° counterclockwise; or in the range 15° to 75°; or in the range 25° to 60°; or in the range of 30° to 50°. The angle of rear surface of handle 117, with respect to device plane 110, may be within the range of 0° to 90° counterclockwise; or in the range 15° to 75°; or in the range 30° to 70°; or in the range of 40° to 60°. Further first and second surfaces 122A and 122B are curved surfaces formed roughly in the plane of the drawing. First surface 22A is cut-away in FIG. 1, and not shown. Second surface 122B shows the rear side of the surface. Surfaces 22A and 22B are both concave, and are surrounded generally by upper surface 115, transition surface 116, handle 117, bottom 118 and the bulb. Within some embodiments of the invention FIG. 1 is to scale whilst in other embodiments of the invention it is not to scale.

Figure 2:
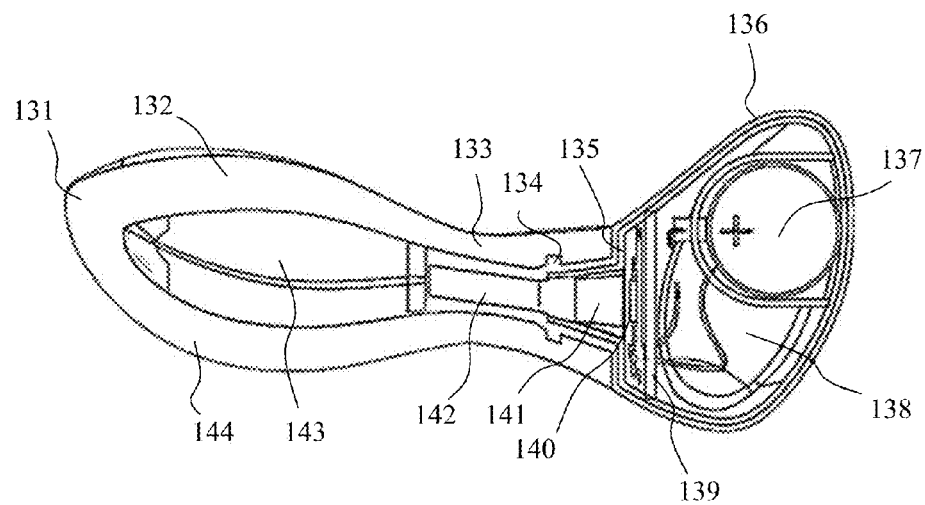
FIG. 2 depicts a cross-section of an adult device according to an embodiment of the invention with major elements identified.

FIG. 2 shows some of the major elements of the device, according to an embodiment of the invention. As depicted there is a tip 131 of the device whilst anterior wall 132 and posterior wall 144 form the pillow with hollow space 143 within it. A recessed key 134 in the pillow mates with the socket key. The pillow mates with socket 136 at pillow-socket joint 135. Within this are battery 137 which fits within the hollow portion 138 the handle, or socket 136. A pressure sensor 140 is mounted to a PCB 139 which contains the internal electronics for the ADDEV. Also indicated are end 141 end of the airway 142 at the pressure sensor 140. Neck 133 of the pillow fits around and is seated upon the 142. Within some embodiments of the invention FIG. 2 is to scale whilst in other embodiments of the invention it is not to scale.

Figure 3:
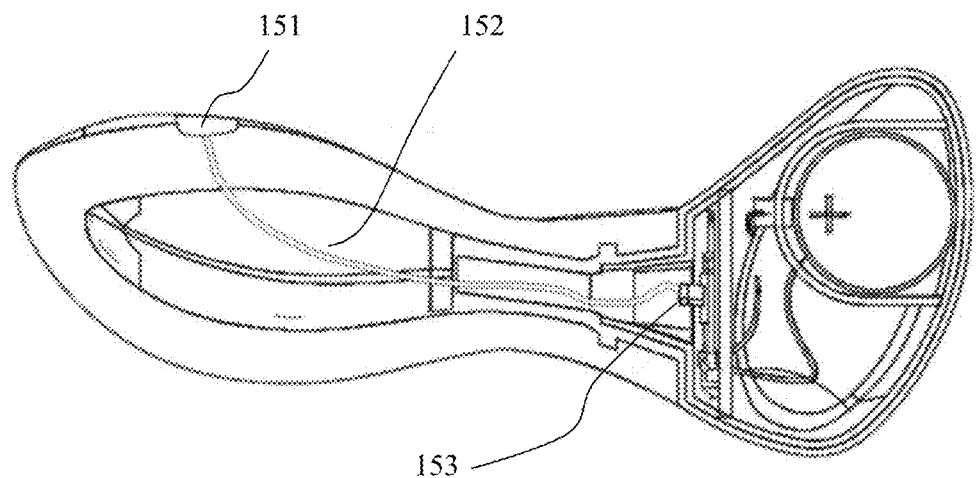
FIG. 3 depicts an adult device according to an embodiment of the invention with additional sensor(s) depicted.

Now referring to FIG. 3 there is depicted an embodiment of the invention with a sensor 151 deployed in the surface of the pillow connected to the PCB via connector 153 and cable 152. Accordingly, one or more sensors may be deployed in the surface of the pillow and coupled to the PCB and/or a second PCB via cables. Subsequently, in respect of FIGS. 12 to 14B other embodiments of the invention are depicted with sensors which are described below wherein their cabling/connectivity may be within the body of the pillow rather than through the hollow chamber(s) within the pillow. For example, FIGS. 12 to 14B may employ a flexible scaffold to which the electrical interconnections and sensors are attached prior to the silicone casing of the ADDEV being formed.

Figure 4:
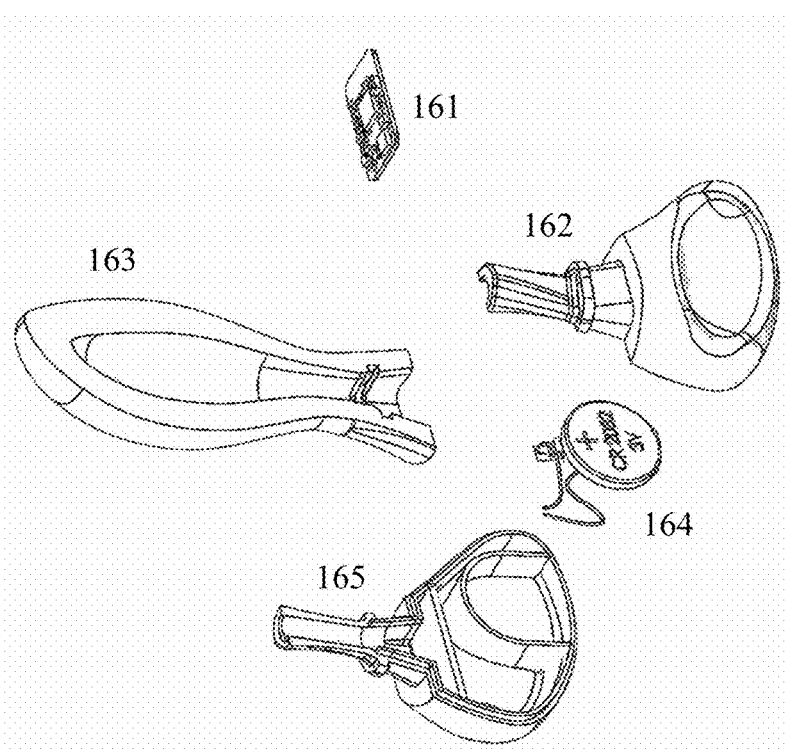
FIG. 4 depicts an exploded view of an adult device according to an embodiment of the invention as depicted in FIGS. 1 and 2 showing the major elements of the device and potential construction methodology.

Referring to FIG. 4 there is depicted an exploded three dimensional (3D) "blown-out" assembly depicted a method of manufacturing an ADDEV according to an embodiment of the invention. Accordingly, there are depicted:
  PCB 161 which is the internal electronics for interfacing to the pressure sensor(s) and/or other sensor(s) wherein in some embodiments of the invention the PCB also includes a wireless antenna such as a Bluetooth Low Energy (BLE) antenna;
  Battery 164 or battery module which may, for example, be sealed within the ADDEV without external connections such that the ADDEV is disposed of once the battery is drained or alternatively there may be an external connection for an electrical power supply to recharge a rechargeable battery 164 or rechargeable battery module;
  Pillow 63 is a cut-away cross-section of what would typically be molded as a single piece part although it may in other embodiments of the invention be formed from two portions;
  Anterior portion 162 of a shell (scaffold) forming the part of the socket (handle) which together with posterior portion 165 forms the rear held portion of the ADDEV; and Posterior portion 165 of a shell (scaffold) forming the part of the socket (handle) which together with anterior portion 162 forms the rear held portion of the ADDEV.

Accordingly, the ADDEV may be assembled by placing the PCB 161 and battery 164 within the posterior and anterior portions 162 and 165 which are attached to one another, for example by virtue of being screwed together, glued together, or joined via snap-fit fixturing for example. Then the pillow 163 is attached to the resulting socket. Optionally, an ADDEV may be sold with multiple pillows of the same geometry such that these may be replaced periodically or these may be of different physical dimensions such that the user can select the one that gives them the best fit/comfort and provides appropriate monitoring of the activity of their muscles, e.g. vaginal muscles. Optionally, a vaginal pillow and an anal pillow may be provided allowing a user to perform exercises and monitor muscle activity/progress for both.

Figure 5:
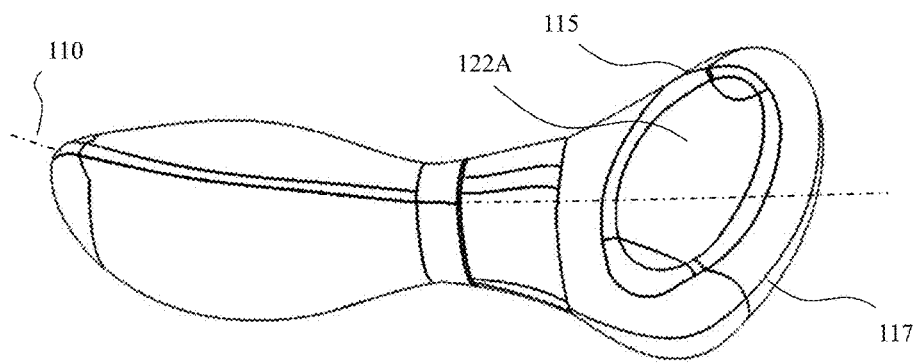
FIG. 5 depicts a 3D rendering of an adult device according to an embodiment of the invention focusing to the grip.
Figure 6A:
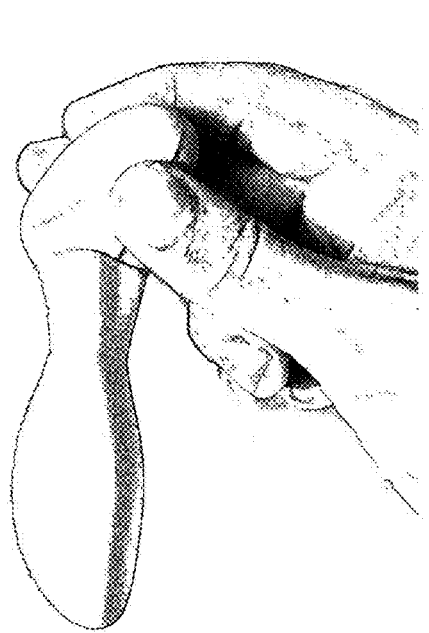
FIGS. 6A and 6B depict a user and another user holding an adult device according to an embodiment of the invention.
Figure 6B:
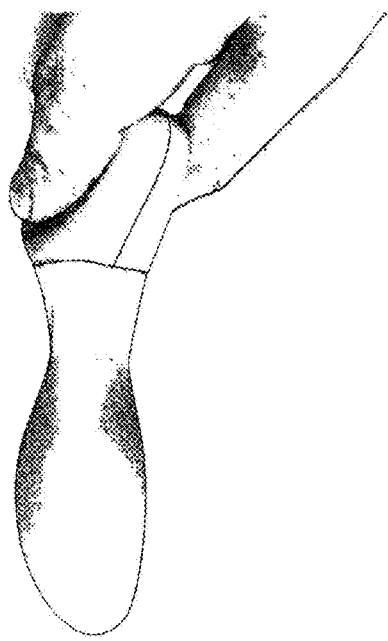

Now referring to FIG. 5 there is depicted a 3D rendering of an embodiment of the invention wherein the asymmetrical shape is evident both spherically and rotationally. The inventors notes that area 122A is an elliptical recess, placed conveniently for the thumb, or thumb and index finger of the user as depicted in FIGS. 6A and 6B respectively. A second area 122B is disposed on the other side of the socket and it is evident that the width and height (along and perpendicular to the device plane 110 are larger than the thickness (posterior to anterior distance). This width to thickness ratio is an improvement over prior art in that it permits the user to easily rotationally adjust the ADDEV once inserted. The firm thumb and fingers grip of the handle not only matches a natural orientation of the hand for placement of the device, but also provides easy and firm adjustment of the depth and orientation of the device. Also depicted ate the rear of the handle 117 and the upper surface 115.

Referring to FIG. 6A there is depicted a typical user grip, with the thumb and index finger grasping the device using upper surface 15 and handle 117, respectively. Referring to FIG. 6B there is depicted what the inventors refer to as a typical physician grip, or that of another user, with the thumb and index finger grasping the device using concave surfaces 122A and 122B.

According to embodiments of the invention there is a narrowing of the neck where the pillow and socket mate which provides for improved comfort and more effective measurements of contractions when a user performs muscle exercises with the ADDEV inserted. Within the prior art, the minimum, average, or maximum compression in this region are too small, either due to a large diameter in this region for designs such as Kegel balls etc. which are typically spherical or ellipsoid in geometry. The diameter according to embodiments of the invention measured from upper neck portion 113 to concave surface 120 (see FIG. 1) may be less 90%, 80%, 70%, 60%, 50%, 45%, 40%, 35%, or 30% of the diameter of the device measured at the largest diameter of the pillow.

Figure 7:
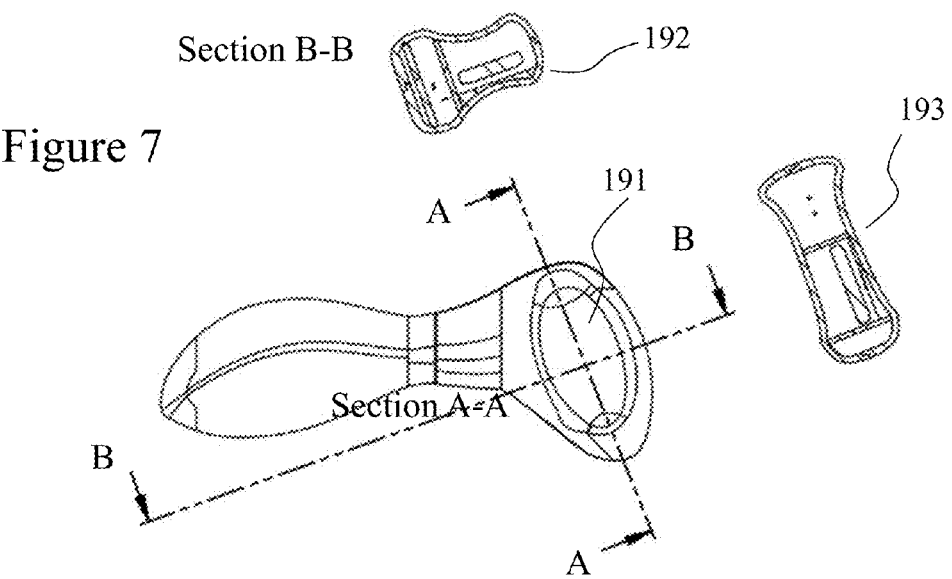
FIG. 7 depicts views of a handle of an adult device according to an embodiment of the invention.
Figure 8:
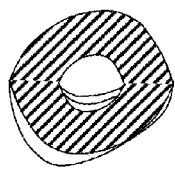
FIG. 8 depicts the asymmetry within an adult device according to an embodiment of the invention through different cross-sections.
Figure 8:
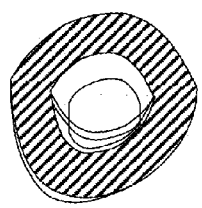
Figure 8:
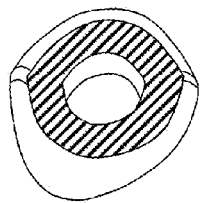
Figure 8:
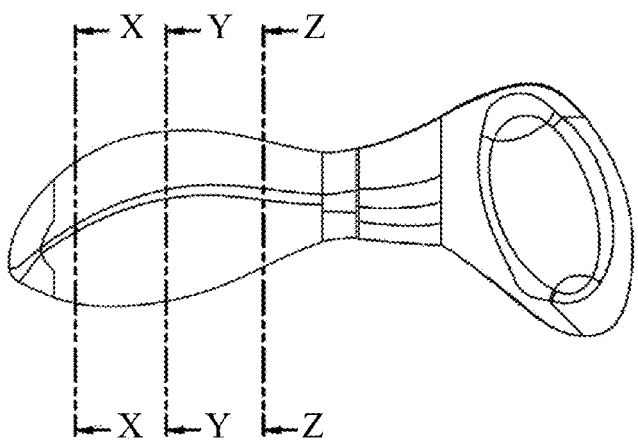

Now referring to FIG. 7 there are depicted first and second cross-sections A-A and B-B respectively of the socket portion of an ADDEV according to an embodiments of the invention. As noted supra there are elliptical recesses 122A/122B on the posterior/anterior portions of the socket adapted to a thumb and to one or two opposing fingers. One side of this elliptical recess is shown as 191. Note that the depth and radius of the two cross-sections A-A and B-B of this recess, shown as cross-sectional views 193 and 192 respectively, are distinctly different. The recess, two opposing recesses, and the elliptical shape of the recess are associated with many embodiments of the invention. The recesses and radii may be as shown in this FIG. 9, or be within the range pictured larger or smaller by plus or minus 10%, 15%, 20%, 25%, 30%, 40%, 50%, 60%, 75%, or 90%, as percentages of the size of the socket. Note that the labeling of these cross sections is not consistent with labeling on other Figures.

Figure 15:
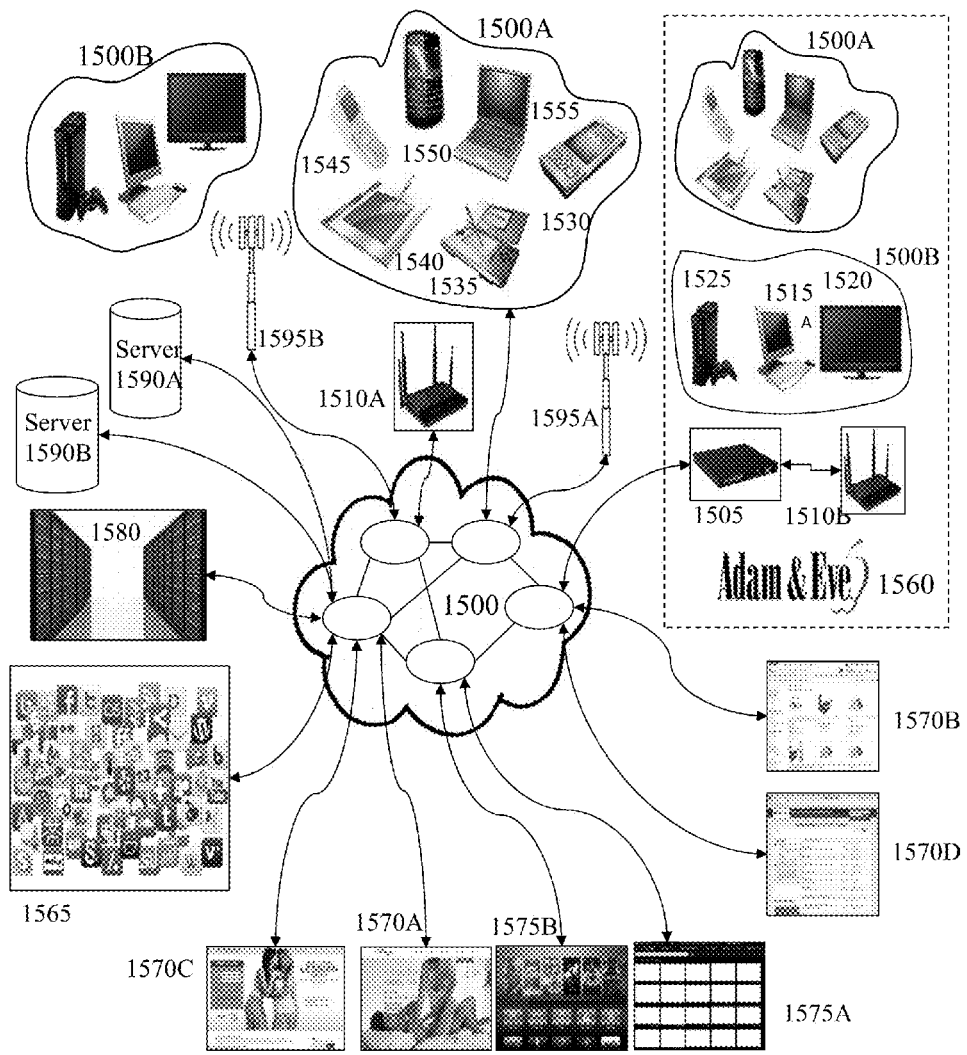
FIG. 15 depicts a network environment within which embodiments of the invention may be employed.

It would also be evident that the center of the grip portion of the socket, shown as the recess 191, is close to the primary axis of the device, shown here and in FIG. 1 as device plane 110. The center of the grip recess of the handle may be within 5 mm, 10 mm, 12.5 mm, 20 mm, 25 mm, 38 mm, 50 mm, or 75 mm o(0.2", 0.5", 0.8", 1", 1.5", 2", or 3") of this axis, device plane 110, or larger. As noted supra an inventive aspect of ADDEVs according to embodiments of the invention is their asymmetry. Looking towards the tip of an ADDEV according to an embodiment of the invention then the left-right width and shape are distinct compared with the posterior-anterior width and shape. In particular the former is wider than the latter, as measured at the widest portions of the bulb on each axis. Referring now to FIG. 15 this asymmetry is depicted for an ADDEV according to an embodiment of the invention through three different cross-sections of the pillow, X-X, Y-Y and Z-Z. Note that the labeling of these cross sections is not consistent with labeling on other Figures.

Within another embodiment of the invention for an ADDEV the cross-section width in the lateral plane may be at least 1.3 times the cross-section width in the ventral-dorsal plane, or the sagittal plane, at cross-sections X-X and Y-Y. Within another embodiment of the invention, at the Y-Y cross section the difference-ratio between the widest and narrowest width at that cross section may be at least 1.05, 1.1, 1.2, 1.3, 1.5, 1.7, 2.0, 2.5, 3.0, 3.5, or 4.0.

Now referring to FIG. 9 there is depicted an ADDEV in side view and cross-sectional side-view 900A and 900B respectively. As evident from side view 900A the pillow 930 and socket 920 are augmented with a clitoral portion 910. As depicted in cross-sectional view 900B the pillow 930 comprises a single air chamber 950 coupled to a pressure sensor 960 which is connected to a battery 980 and control circuit 970. The battery 980 being coupled to a power socket 990 allowing the battery 980 to be recharged. Optionally, rather than employing a wireless interface the ADDEV may employ a wired data connection routed through power/data socket 990 such as a micro-USB or Apple™ Lightning for example. Also connected to the controller is vibrating element 940. Accordingly, the ADDEV depicted in FIG. 9 may be employed as a vaginal muscle exercise device wherein completion of a predetermined training schedule or activity results in the activation of the vibratory function for the user's clitoris. Alternatively, the vibratory function of the vibrating element 940 may be activated in response to each muscle flexure or action performed by the user so that the more they exercise within a given session the longer the vibratory element 940 provides stimulation to the user's clitoris.

Figure 10:
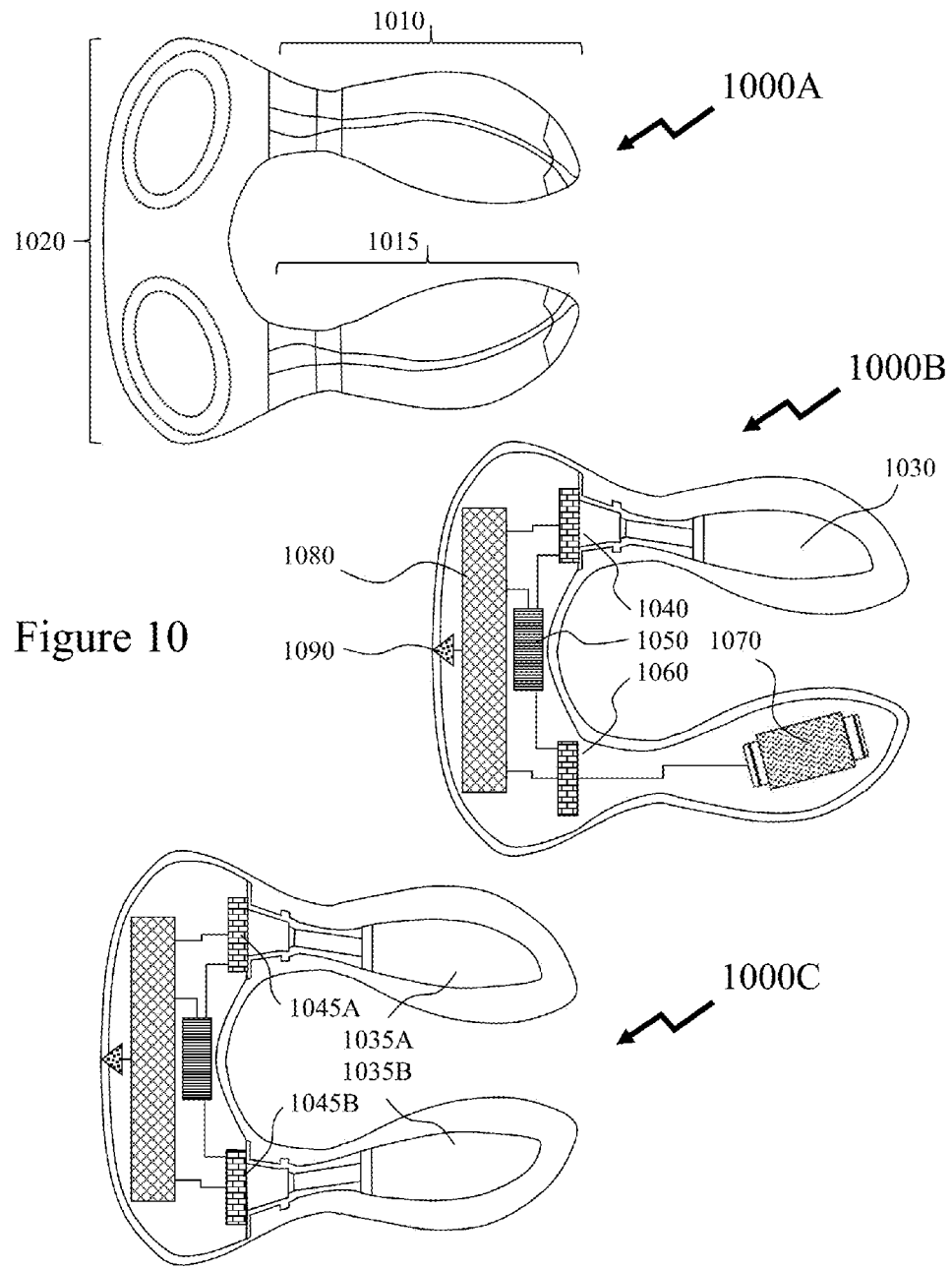
FIG. 10 depicts a side view and two cross-sectional side views of an adult device according to an embodiment of the invention with vaginal and anal elements.

Now referring to FIG. 10 there is depicted an ADDEV in side view 1000A together with first and second cross-sectional side-views 1000B and 1000C respectively. As evident from side view 1000A the vaginal pillow 1010 and socket are now augmented with anal pillow 1015 and a larger socket 1020 encompassing two grip regions. As depicted in first cross-sectional view 1000B the vaginal pillow comprises a single air chamber 1030 coupled to a pressure sensor 1040 which is connected to a battery 1080 and control circuit 1050. The battery 1080 being coupled to a power socket 1090 allowing the battery 1080 to be recharged. Optionally, rather than employing a wireless interface the ADDEV may employ a wired data connection routed through a power/data socket 1090 such as a micro-USB or Apple™ Lightning for example. The controller 1050 is also coupled to a second circuit 1060 which provides control and power to vibratory element 1070 within the anal portion 1015. Accordingly, the ADDEV depicted in FIG. 10 in first cross-section 1000B may be employed as a vaginal muscle exercise device wherein completion of a predetermined training schedule or activity results in the activation of the vibratory function for the user's anus. Alternatively, the vibratory function of the vibrating element 1070 may be activated in response to each muscle flexure or action performed by the user so that the more they exercise within a given session the longer the vibratory element 1070 provides stimulation to the user's anus.

As depicted in second cross-sectional view 1000C the vaginal pillow comprises a first air chamber 1035A coupled to a first pressure sensor 1045A which is connected to the battery and control circuit as discussed supra in respect of first cross-section 1000B. However, in this embodiment of the invention the control circuit is also coupled to second pressure sensor 1045B which is coupled to the second air chamber 1035B within the anal pillow 1015. Accordingly, the ADDEV allows a user to perform vaginal and anal muscle training/exercises with a single device. Within embodiments of the invention the vaginal and anal pillows 1010 and 1015 may be the same, similarly or dimensioned differently. Wherein they are dimensioned similarly or the same then through the use of an accelerometer circuit within the ADDEV to determine orientation it is feasible for the user to employ an ADDEV such as depicted in second cross-section 1000C in either orientation leading to the socket having dual grip elements that are the mirror image of each other.

Optionally, within another embodiment of the invention the anal pillow may be coupled not only to a pressure sensor but also a fan and partial non-return valve such that the anal pillow can be partially inflated, for example, in response to correct vaginal muscle exercises. The inventors define the term "partial non-return valve" as once the fan stops blowing then the anal pillow 1015 will deflate slowly allowing its removal once it has returned to or close to its original dimensions. Optionally, the non-return valve may be electronically controlled in other embodiments of the invention in conjunction with a mechanical pump. Alternatively, the anal pillow 1015 may be part of a self-contained fluidic actuation and control system within the ADDEV such that a reservoir within the socket provides fluid to inflate elements within the anal pillow or the anal pillow directly.

Figure 11B:
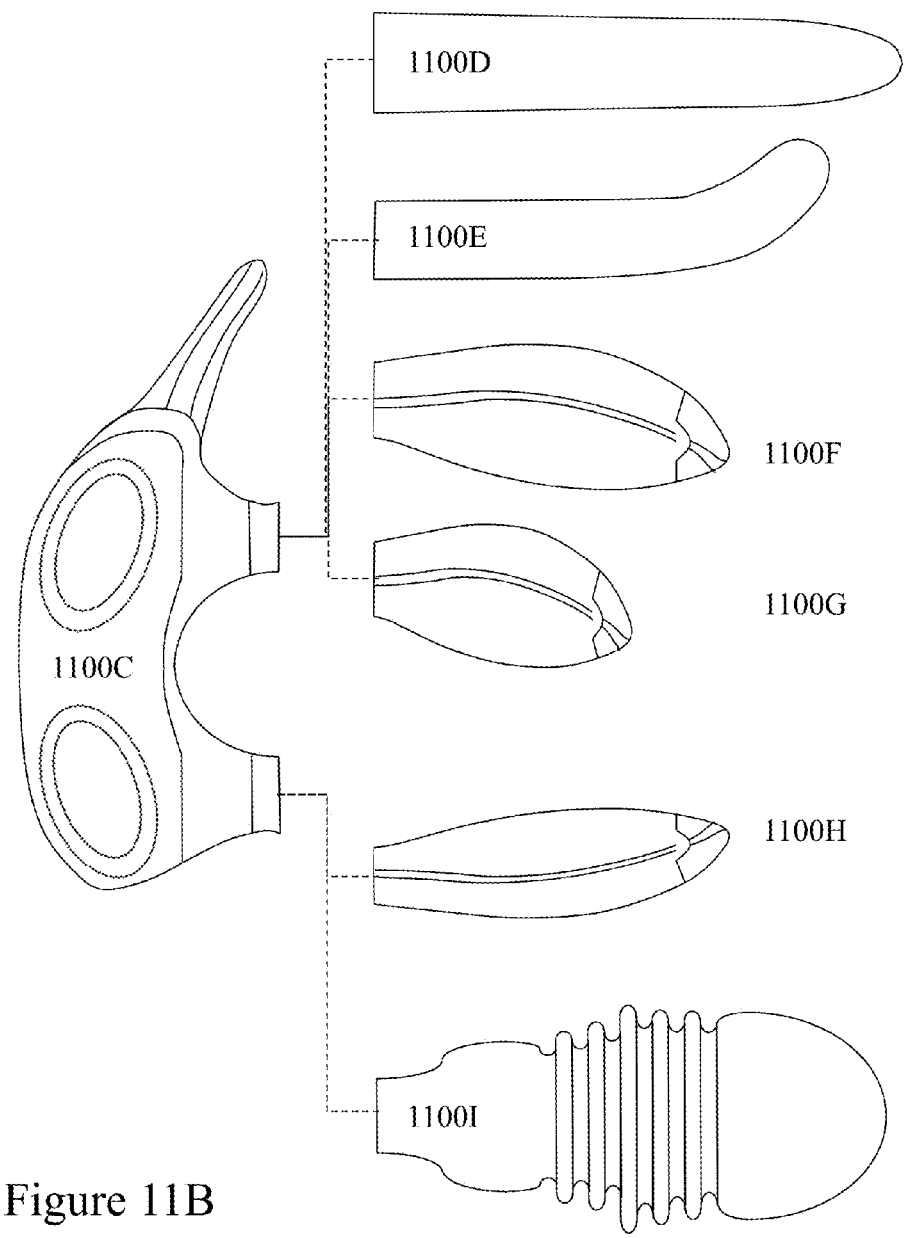
FIG. 11B depicts side views of an adult device according to an embodiment of the invention with changeable vaginal and/or anal elements together with a clitoral stimulator.

Now referring to FIG. 11 there is depicted an ADDEV in side view 1100A together with cross-sectional side-view 1100B respectively. As evident from side view 1100A the vaginal pillow 1120 and socket are now augmented with anal pillow 1125, clitoral portion 1110 and a larger socket 1130 encompassing two grip regions. As depicted in first cross-sectional view 1100B the vaginal pillow comprises a single air chamber 1160 coupled to a pressure sensor integrated with first circuit 1150 which is connected to a battery 1190 and control circuit 1180. The battery 1190 being coupled to a power socket 1195 allowing the battery 1190 to be recharged. Optionally, rather than employing a wireless interface the ADDEV may employ a wired data connection routed through a power/data socket 1190 such as a micro-USB or Apple™ Lightning for example. The controller 1180 is also coupled to a second circuit 1150 which controls a first vibrating element 1170 and to a second vibrating element 1140 within the clitoral portion 1140 via the first circuit 1150. Accordingly, it is evident as described supra that the functionality of the first vibrating element 1170 and second vibrating element 1140 may be established in dependence upon a mode of the ADDEV, e.g. sex toy or muscle exerciser, and that within a selected mode the characteristics of the first and second vibrating elements 1140 and 1170 may be adjusted in dependence upon a variety of factors including, but not limited, user input, user progress, clinical or personal use, etc. Further, as discussed below the first and second vibrating elements 1140 and 1170 may be adjusted in dependence upon direct measurements of the user such as sexual arousal, sexual wellness etc.

Optionally, the ADDEVs depicted in FIGS. 9 to 11A may be augmented further by making the pillow to socket connection demountable such that the user can replace, for example, a vaginal exerciser pillow with a 150 mm (6") Gräfenberg spot (G-spot) vibrator or the anal exerciser pillow can be replaced with a 75 mm long by 50 mm diameter butt plug. Such a reconfigurable ADDEV is depicted within FIG. 11B wherein mountable to the socket 1100C are:

straight dildo/vibrator element 1100D;
curved G-spot dildo/vibrator element 1100E;
"large" pillow 1100F;
"small" pillow 1100G;
"thin long" pillow 1100H; and
butt plug 11001.

It was briefly discussed supra in respect of FIG. 3 that additional sensors may be integrated with an ADDEV according to an embodiment of the invention. Referring to FIGS. 12 to 14A there are depicted examples of additional sensors relating to sexual wellness and/or sexual arousal determination. Accordingly referring to FIG. 12 with first and second cross-sections 1200A and 1200B respectively there are depicted deployment scenarios in respect of labial thermistors wherein increased blood flow to the labia results in an increase in the temperature of the labia which via the temperature dependent resistance of the thermistors can be monitored. Accordingly, in first cross-section 1200A first and second labial thermistors 1210 and 1220 are disposed within the region of the pillow-socket coupling for a discrete pillow device whereas in second cross-section 1200B third and fourth labial thermistors 1230 and 1240 are depicted within a device such as those depicted within FIGS. 9 and 11A respectively wherein labial thermistor 1230 is extended around the surface of the ADDEV for improved coupling the upper pelvic region between their clitoris and vagina. Fourth labial thermistor 1240 is depicted on the lower edge of the user's vaginal opening. Optionally, the thermistors may be disposed on the sides of the ADDEV elements rather than the surfaces directly in engagement with the user's body. Accordingly, as the user uses their ADDEV for sexual stimulation and/or vaginal exercises their labial temperature can be monitored for an indication of sexual arousal allowing adjustment of control program parameters, control settings, feedback from vaginal exercise etc. Optionally, extended monitoring of the user's labial temperature discretely or in conjunction with other biometric data may allow automatic determination of the user's menstrual cycle and subsequent projections as to the user's menstrual cycle from recent temperature trend data correlated to historical data. Optionally, the user may enter data to align the acquired data with their menstrual cycle. Optionally, within other embodiments of the invention the thermistor may be replaced by another element with an electrical characteristic that is temperature dependent such as resistance, inductance, or capacitance for example.

Figure 13:
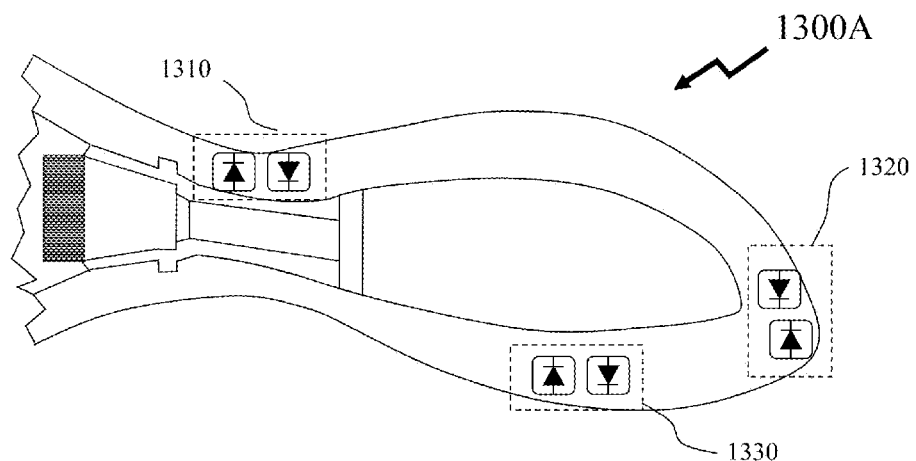
FIG. 13 depicts portions of an adult device according to an embodiment of the invention depicting additional optical emitter/detector elements for arousal monitoring via laser Doppler imaging and photoplethysmography.
Figure 13:
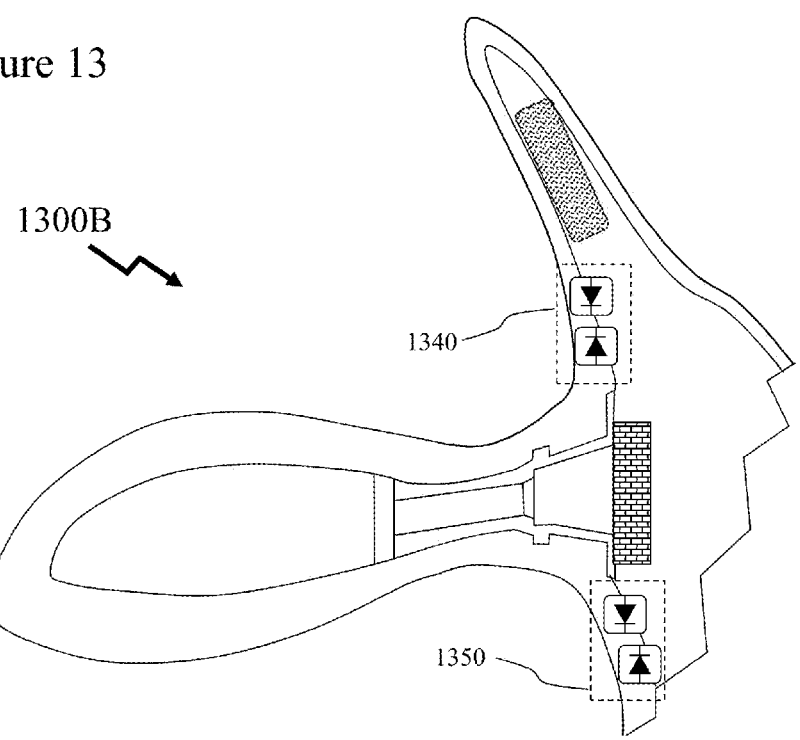

Now referring to FIG. 13 there are depicted with first and second cross-sections 1300A and 1300B respectively there are depicted deployment scenarios in respect of optical sensor elements for determining, for example, labial and vaginal blood flow using photoplethysmography (PPG) and/or laser Doppler imaging (LDI). Accordingly, in first cross-section 1200A first to third Optical Source and Detector (OSAD) pairs 1310 to 1330 are depicted disposed within the pillow of a discrete pillow device. As depicted first OSAD pair 1310 is towards the upper vaginal opening on the pillow-socket region of the ADDEV, second OSAD pair 1320 towards the cervix at the tip of the pillow and third OSAD pair 1330 on the lower vaginal wall within the pillow. In second cross-section 1300B fourth and fifth OSAD pairs 1340 and 1350 are depicted within a device such as those depicted within FIGS. 9 and 11A respectively wherein the fourth and fifth OSAD pairs 1340 and 1350 are within the extended socket surface of the ADDEV for improved coupling the upper pelvic region between their clitoris and vagina and lower pelvic region between vagina and anus. Within PPG exploiting a reflective mode as depicted the volume of blood is determined in dependence upon the intensity of the reflected whilst each cardiac cycle appears as a peak within the reflected signal. As blood flow to the skin can be modulated by multiple other physiological systems, PPG can also be used to monitor breathing (respiration), medication effects, hypovolemia, and other circulatory conditions, especially where extended monitoring under a variety of conditions including rest and/or sleep provide enhanced baseline and/or early data. For example, the height of AC component of the PPG is proportional to the pulse pressure, the difference between the systolic and diastolic pressure in the arteries. Additionally, the shape of the PPG waveform differs from subject to subject, and varies with the location, providing additional options such as identification of user through PPG data and automatic adjustment of the ADDEV parameters/control program etc. in response therefrom.

Alternatively, the OSAD pair may be employed for laser Doppler imaging (LDI) wherein the OSAD is typically an infrared laser source in conjunction with a photodetector rather than a visible LED and photodetector in the instance of PPG. Accordingly, the pulsed laser light interacts with moving blood cells such that a small portion of it is reflected with a frequency shift, detected, and converted into an electrical signal. LDI can provide a direct measure of female sexual response in that it does not require physical contact and the signals are typically acquired at depth of 2-3 mm (approx. ⅛") below the skin surface. It would be evident that one, two or more OSAD pairs may be employed and that their position may vary according to the design of the ADDEV and/or pillow including, for example, laterally disposed on the ADDEV or disposed in respect of the clitoris, etc.

Figure 14A:
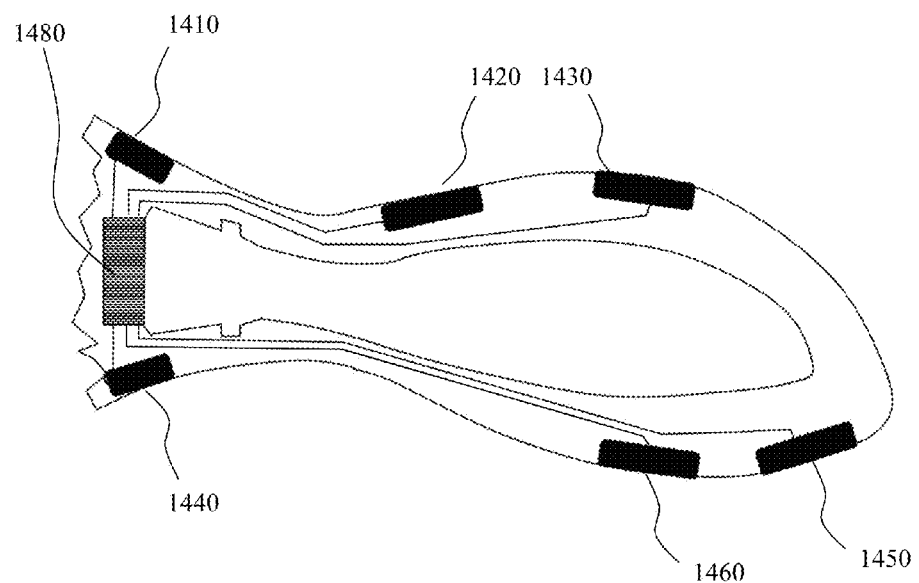
FIG. 14A depicts a portion of an adult device according to an embodiment of the invention depicting additional electrical contacts and acoustic sensors for arousal monitoring and sexual wellness monitoring.

Now referring to FIG. 14A there is depicted a pillow for an ADDEV according to an embodiment of the invention wherein multiple electrical contacts are disposed. As depicted there are first to third contact pairs 1410/1440; 1420/1430; and 1450/1460 of electrical contacts (ELCOs) connected to circuit 1480. It would be evident that one, two or more ELCO pairs may be employed and that their position may vary according to the design of the ADDEV and/or pillow including, for example, laterally disposed on the ADDEV or disposed in respect of the clitoris, etc. Equally, an array of ELCOs may be employed as well as a discrete ELCO and/or spatially separated ELCO pair(s). An ELCO may be employed to measure electrical activity and/or provide electrical stimulation to the user's vagina/anus/clitoris according to the design of the ADDEV and their disposition on the ADDEV. Accordingly, the device may provide electrostimulation of the vaginal muscles with part of an exercise/training regime and then determine from user flexing the muscle strength/range of motion etc.

Within an alternate embodiment of the invention one or more of the ELCO elements may be replaced with a microphone such as one based upon capacitive thin film or microelectromechanical systems (MEMS) transducer, a piezoelectric transducer, accelerometer, hydrophone, or another type of microphone in order to measure the acoustic output of a contracting muscle. Accordingly, based upon such microphone placement an ADDEV according to an embodiment of the invention may support acoustic myography (AMG) of the pubococcygeus muscle and/or other of the pelvic floor muscles. Beneficially, the pillow geometry enhances/assures contact of one or more microphone to an inner surface of the vagina or the cervix. Typically, AMG has a frequency range of interest that is primarily 5-50 Hz, although there is value beyond this range which beneficially are captured by the microphone sensor, particularly, in the upper portion of this frequency range, whilst the pressure sensor detects a lower portion of the frequency range. Within other embodiments of the invention the microphone may be reversed to function as a loudspeaker or a dedicated loudspeaker element may be provided such that the ADDEV provides acoustic stimulation directly such as that derived from music, video, broadcast television, multimedia etc.

Figure 14B:
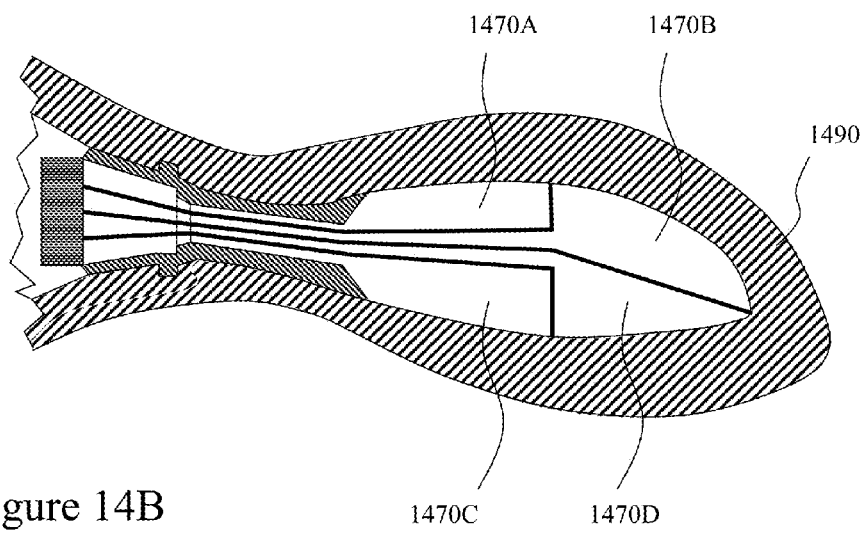
FIG. 14B depicts a portion of an adult device according to an embodiment of the invention depicting partitioning to four chambers.

Within the embodiments of the invention described and depicted in respect of FIGS. 1 to 14A the pillow has been depicted with a single chamber. However, it would be evident that the chamber may in other embodiments of the invention be partitioned through flexible and/or inflexible membranes. An example of such a multi-chamber pillow is depicted in FIG. 14B wherein the pillow 1490 is divided into four chambers 1470A to 1470D which are depicted as upper rear/upper front/lower rear and lower front respectively. However, within other embodiments of the invention the chambers may be "radially" positioned such as quadrants of the length of the pillow or simply upper/lower of upper/lower/tip etc.

Figure 16:
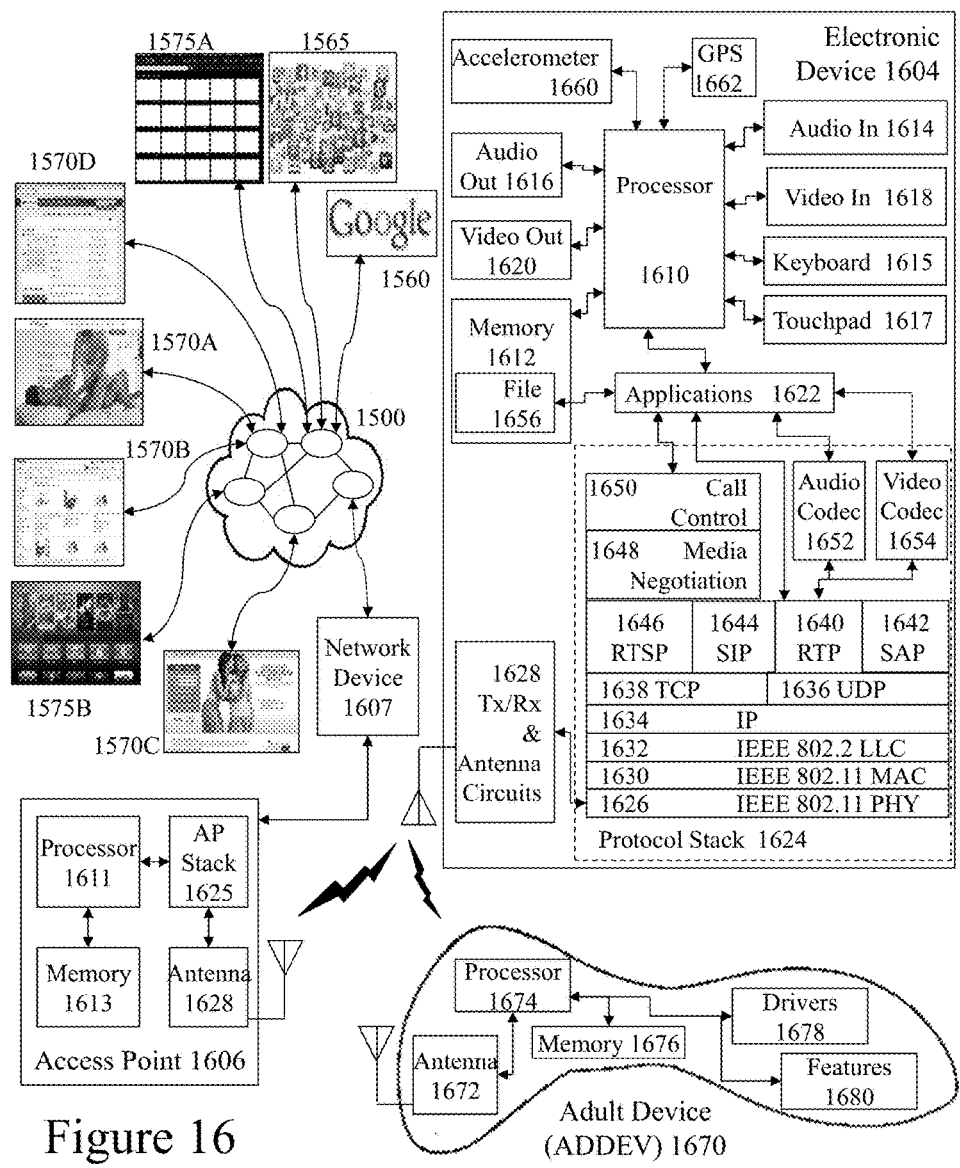
FIG. 16 depicts a wireless portable electronic device supporting communications to a network such as depicted in FIG. 15 and as supporting embodiments of the invention with respect to adult devices.

Within the descriptions supra in respect of FIGS. 1 to 14B ADDEVs according to embodiments of the invention have been described with respect to providing simulation and assessment of a user's vagina and/or anus and/or clitoris. Electrical control and monitoring have been described together with wired and wireless data connectivity of the ADDEV to the external world. Accordingly, the ADDEV may be wirelessly connected to a user's PED or FED such as depicted in FIG. 16 and access/post content/data to one or more local and/or remote servers associated with different aspects of the user including, but not limited to, their personal ADDEV profile, personal health records, other PEDs/FEDs/wearables, physician's office, etc. Accordingly, the network interconnectivity and structure of a network supporting ADDEVs according to embodiments of the invention are described in respect of FIG. 15 whilst the local device structure, PED/access point (AP) association and network connectivity are described and depicted in respect of FIG. 16.

Referring to FIG. 15 there is depicted a network environment 1500 within which embodiments of the invention may be employed supporting ADDEV systems, applications, and platforms (ADSAPs) according to embodiments of the invention. Such ADSAPs, for example supporting multiple channels and dynamic content. As shown first and second user groups 1500A and 1500B respectively interface to a telecommunications network 1500. Within the representative telecommunication architecture a remote central exchange 1580 communicates with the remainder of a telecommunication service providers network via the network 1500 which may include for example long-haul OC-48/OC-192 backbone elements, an OC-48 wide area network (WAN), a Passive Optical Network, and a Wireless Link. The central exchange 1580 is connected via the network 1500 to local, regional, and international exchanges (not shown for clarity) and therein through network 1500 to first and second cellular APs 1595A and 1595B respectively which provide Wi-Fi cells for first and second user groups 1500A and 1500B respectively. Also connected to the network 1500 are first and second Wi-Fi nodes 1510A and 1510B, the latter of which being coupled to network 1500 via router 1505. Second Wi-Fi node 1510B is associated with Enterprise 1560, such as Adam & Eve™ for example, within which other first and second user groups 1500A and 1500B are disposed. Second user group 1500B may also be connected to the network 1500 via wired interfaces including, but not limited to, DSL, Dial-Up, DOCSIS, Ethernet, G.hn, ISDN, MoCA, PON, and Power line communication (PLC) which may or may not be routed through a router such as router 1505.

Within the cell associated with first AP 1510A the first group of users 1500A may employ a variety of PEDs including for example, laptop computer 1555, portable gaming console 1535, tablet computer 1540, smartphone 1550, cellular telephone 1545 as well as portable multimedia player 1530. Within the cell associated with second AP 1510B are the second group of users 1500B which may employ a variety of FEDs including for example gaming console 1525, personal computer 1515 and wireless/Internet enabled television 1520 as well as cable modem 1505. First and second cellular APs 1595A and 1595B respectively provide, for example, cellular GSM (Global System for Mobile Communications) telephony services as well as 3G and 4G evolved services with enhanced data transport support. Second cellular AP 1595B provides coverage in the exemplary embodiment to first and second user groups 1500A and 1500B. Alternatively the first and second user groups 1500A and 1500B may be geographically disparate and access the network 1500 through multiple APs, not shown for clarity, distributed geographically by the network operator or operators. First cellular AP 1595A as show provides coverage to first user group 1500A and environment 1570, which comprises second user group 1500B as well as first user group 1500A. Accordingly, the first and second user groups 1500A and 1500B may according to their particular communications interfaces communicate to the network 1500 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-1000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly portable electronic devices within first user group 1500A may form associations either through standards such as IEEE 802.15 and Bluetooth as well in an ad-hoc manner.

Also connected to the network 1500 are Social Networks (SOCNETS) 1565, ADDEV manufacturer 1570A, e.g. We-Vibe™ by Standard Innovation Corporation; online retailer 1570B, e.g. Amazon™; online personals website 1570C, e.g. PinkCupid™; online chat/discussion/bulletin board/forum 1570D, e.g. www.sexforums.com; adult multimedia content website 1575A, e.g. RedTube™; and multimedia content website 1575B, e.g. iTunes™; as well as first and second servers 1590A and 1590B which together with others, not shown for clarity. Accordingly, a user employing one or more ADSAPs may interact with one or more such providers, enterprises, service providers, retailers, third parties etc. and other users. First and second servers 1590A and 1590B may host according to embodiments of the inventions multiple services associated with a provider of ADDEV systems, applications, and platforms (ADSAPs); a provider of a SOCNET or Social Media (SOME) exploiting ADSAP features; a provider of a SOCNET and/or SOME not exploiting ADSAP features; a provider of services to PEDS and/or FEDS; a provider of one or more aspects of wired and/or wireless communications; an Enterprise 1560 exploiting ADSAP features; license databases; content databases; image databases; content libraries; customer databases; websites; and software applications for download to or access by FEDs and/or PEDs exploiting and/or hosting ADSAP features. First and second primary content servers 1590A and 1590B may also host for example other Internet services such as a search engine, financial services, third party applications and other Internet based services.

Accordingly, a user may exploit a PED and/or FED within an Enterprise 1560, for example, and access one of the first or second primary content servers 1590A and 1590B respectively to perform an operation such as accessing/downloading an application which provides ADSAP features according to embodiments of the invention; execute an application already installed providing ADSAP features; execute a web based application providing ADSAP features; or access content. Similarly, a user may undertake such actions or others exploiting embodiments of the invention exploiting a PED or FED within first and second user groups 1500A and 1500B respectively via one of first and second cellular APs 1595A and 1595B respectively and first Wi-Fi nodes 1510A.

Now referring to FIG. 16 there is depicted an electronic device 1604 and network access point 1607 supporting ADSAP features according to embodiments of the invention. Electronic device 1604 may, for example, be a PED and/or FED and may include additional elements above and beyond those described and depicted. Also depicted within the electronic device 1604 is the protocol architecture as part of a simplified functional diagram of a system 1600 that includes an electronic device 1604, such as a smartphone 1555, an access point (AP) 1606, such as first AP 1510, and one or more network devices 1607, such as communication servers, streaming media servers, and routers for example such as first and second servers 1590A and 1590B respectively. Network devices 1607 may be coupled to AP 1606 via any combination of networks, wired, wireless and/or optical communication links such as discussed above in respect of FIG. 15 as well as directly as indicated. Network devices 1607 are coupled to network 1500 and therein Social Networks (SOCNETS) 1565, ADDEV manufacturer 1570A, e.g. We-Vibe™ by Standard Innovation Corporation; online retailer 1570B, e.g. Amazon™; online personals website 1570C, e.g. PinkCupid™; online chat/discussion/bulletin board/forum 1570D, e.g. www.sexforums.com; adult multimedia content website 1575A, e.g. RedTube™; and multimedia content website 1575B, e.g. iTunes™.

The electronic device 1604 includes one or more processors 1610 and a memory 1612 coupled to processor(s) 1610. AP 1606 also includes one or more processors 1611 and a memory 1613 coupled to processor(s) 1610. A non-exhaustive list of examples for any of processors 1610 and 1611 includes a central processing unit (CPU), a digital signal processor (DSP), a reduced instruction set computer (RISC), a complex instruction set computer (CISC) and the like. Furthermore, any of processors 1610 and 1611 may be part of application specific integrated circuits (ASICs) or may be a part of application specific standard products (ASSPs). A non-exhaustive list of examples for memories 1612 and 1613 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

Electronic device 1604 may include an audio input element 1614, for example a microphone, and an audio output element 1616, for example, a speaker, coupled to any of processors 1610. Electronic device 1604 may include a video input element 1618, for example, a video camera or camera, and a video output element 1620, for example an LCD display, coupled to any of processors 1610. Electronic device 1604 also includes a keyboard 1615 and touchpad 1617 which may for example be a physical keyboard and touchpad allowing the user to enter content or select functions within one of more applications 1622. Alternatively the keyboard 1615 and touchpad 1617 may be predetermined regions of a touch sensitive element forming part of the display within the electronic device 1604. The one or more applications 1622 that are typically stored in memory 1612 and are executable by any combination of processors 1610. Electronic device 1604 also includes accelerometer 1660 providing three-dimensional motion input to the process 1610 and GPS 1662 which provides geographical location information to processor 1610.

Electronic device 1604 includes a protocol stack 1624 and AP 1606 includes a communication stack 1625. Within system 1600 protocol stack 1624 is shown as IEEE 802.11 protocol stack but alternatively may exploit other protocol stacks such as an Internet Engineering Task Force (IETF) multimedia protocol stack for example. Likewise AP stack 1625 exploits a protocol stack but is not expanded for clarity. Elements of protocol stack 1624 and AP stack 1625 may be implemented in any combination of software, firmware and/or hardware. Protocol stack 1624 includes an IEEE 802.11-compatible PHY module 1626 that is coupled to one or more Tx/Rx & Antenna Circuits 1628, an IEEE 802.11-compatible MAC module 1630 coupled to an IEEE 802.2-compatible LLC module 1632. Protocol stack 1624 includes a network layer IP module 1634, a transport layer User Datagram Protocol (UDP) module 1636 and a transport layer Transmission Control Protocol (TCP) module 1638. Protocol stack 1624 also includes a session layer Real Time Transport Protocol (RTP) module 1640, a Session Announcement Protocol (SAP) module 1642, a Session Initiation Protocol (SIP) module 1644 and a Real Time Streaming Protocol (RTSP) module 1646. Protocol stack 1624 includes a presentation layer media negotiation module 1648, a call control module 1650, one or more audio codecs 1652 and one or more video codecs 1654. Applications 1622 may be able to create maintain and/or terminate communication sessions with any of devices 1607 by way of AP 1606.

Typically, applications 1622 may activate any of the SAP, SIP, RTSP, media negotiation and call control modules for that purpose. Typically, information may propagate from the SAP, SIP, RTSP, media negotiation and call control modules to PHY module 1626 through TCP module 1638, IP module 1634, LLC module 1632 and MAC module 1630. It would be apparent to one skilled in the art that elements of the electronic device 1604 may also be implemented within the AP 1606 including but not limited to one or more elements of the protocol stack 1624, including for example an IEEE 802.11-compatible PHY module, an IEEE 802.11-compatible MAC module, and an IEEE 802.2-compatible LLC module 1632. The AP 1606 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module. Portable and fixed electronic devices represented by electronic device 1604 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-1000, DSL, Dial-Up, DOCSIS, Ethernet, G.hn, ISDN, MoCA, PON, and Power line communication (PLC).

Also depicted is ADult DEVice (ADDEV) 1670 which is coupled to the electronic device 1604 through a wireless interface between Antenna 1672 and Tx/Rx & Antenna Circuits 1628 wherein the electronic device 1604 may support, for example, a national wireless standard such as GSM together with one or more local and/or personal area wireless protocols such as IEEE 802.11 a/b/g WiFi, IEEE 802.16 WiMAX, and IEEE 802.15 Bluetooth for example. The Antenna 1672 is connected to Processor 1674 and therein to Memory 1676, Drivers 1678, and Features 1680. Accordingly, the ADDEV 1670 may operate as standalone device with factory installed control routines accessed through an interface on the ADDEV 1670, not shown for clarity, or through an application in execution upon the electronic device 1604. Subsequently, as described below one or more of these control routines may be modified, amended, deleted etc. whilst other new control routines may be created, acquired, installed etc.

Accordingly it would be evident to one skilled the art that the ADDEV 1670 with associated electronic device 1604 may accordingly download original software and/or revisions for a variety of functions supported by the drivers 1678 and/or features 1680. In some embodiments of the invention the functions may not be implemented within the original as sold ADDEV 1670 and are only activated through a software/firmware revision and/or upgrade either discretely or in combination with a subscription or subscription upgrade for example.

Within the process of determining pelvic floor muscle pressure measurements the user's body position has two impacts. First, the neutral, or relaxed, pressure in the device varies by body position. Second, the maximum pressure for a given muscle strength also varies by body position. Thus, accurate measurements and consistent tracking of performance improvement requires either knowing the user's body position, or requires that the user perform all exercises in the same body position. Determining body position is beneficial and may be established through the employment of an accelerometer or accelerometers within the ADDEV.

In other embodiment, the accelerometer may be used to determine improper exercise technique, such as the use of incorrect muscles, or additional muscles, or a wrong position of the device or the user. In another embodiment, the accelerometer is used to determine pelvic lift with contractions which where automatically determined represents an advancement over the prior art. Within embodiments of the invention a representation of the user's body position may be provided to a FED/PED together with a target body position allowing the user to achieve the required posture/position for the exercise. These depictions of user and target positions may adjust in real time. Similarly, the user may be presented via a PED/FED with a depiction of the user's pelvic floor lift which again may be tracked/monitored/displayed in real time.

In other embodiments, an accelerometer may be used to detect and monitor exercises other than pelvic floor muscle exercises (commonly referred to as Kegel exercises or Kegels), such as leg lifts, hip raises, crunches, oblique crunches, adductor contractions, other core exercises, and other exercises.

Within embodiments of the invention the ADDEV contains one or more sensors including, but not limited to, accelerometer, thermometer, LDI, PPG, and a microphone. This or these may be employed to determine heart rate, menstrual cycle, amount of exercise, changes in physical activity level during an exercise session. Optionally, additional sensors such as a humidity sensor may be incorporated into the device or additional biometric data may be acquired through an aggregator ADSAP such as the user's smart phone for example communicating with the ADDEV and one or more wearable devices. Accordingly, the ADSAP and/or ADDEV can establish whether the user is performing activities such as showering when using the ADDEV as well as detecting cleaning, with the option of powering down the ADDEV in either instance.

In some embodiments of the invention, various detections, determinations, tracking and storage of aspects and parameters, as discussed herein, are executed wholly or partially internally in the ADDEV; in other embodiments they are executed wholly or partially in a wirelessly connected standard user interface running software as part of this embodiment; in yet another embodiment they are executed whole or partially by software running remotely upon remote servers or "in the cloud" as colloquially known. In other embodiments the user may be prompted through such a wirelessly connected standard user interface to perform one or more specific actions in isolation and/or in combination with a view to improving or mitigating an aspect of the user's physiological and/or sexual wellness.

In some embodiments of the invention, current exercise parameters and the user's performance/progress are sent to a doctor, trainer or therapist in real-time and/or periodically. In some embodiments of the invention the doctor, trainer or therapist may concurrently within a communication link, such as a phone call, in the reverse direction provide human, personalized instruction, communication, status, or motivation to the user.

In some embodiments of the invention, current exercise parameters are sent to software in the cloud in real-time; while concurrently a communication link, such as a phone call or browser-based data, in the reverse direction from the cloud software to the user, provides automated, personalized instruction, communication, status, or motivation to the user. Such information from the cloud to the user may include information about the status or progress of other users. Alternatively, based upon the users historical data and their current performance/activity a remote automated analysis and control application may adjust settings within an ADSAP directing the user to perform specific actions and/or exercise and/or direct the user to perform a different exercise regime. Optionally, the user's progress with respect to vaginal muscle control etc. may be correlated with other sexual activity data derived from one or more ADDEVs and/or user's feedback/social media/etc.

In one embodiment, a "pairing code" may be used to enable wireless pairing or a communication link. This paring code may be used for setup, such as with Bluetooth or Bluetooth Low Energy (BLE), or may function as a password for regular or repetitive connectivity. Such a pairing code may comprise a tap sequence, shake sequence, squeeze sequence, orientation of the device, or any combination. Note that any such squeezing may be done by the user's hand, prior to insertion, or by the user's pelvic floor muscles after insertion. Such a pairing code may be used to insure privacy of the user's data. Such protected data may be in the device, in a user interface device, in the cloud, or in any combination. In some embodiments of the invention the user's interface device displays a "challenge", a sequence of actions, such as taps, shacks or orientation, which the user must then perform as a "response" with the device, to enable pairing or the enabling of some application functionality.

Within some embodiments of the invention, simply using the device intra-vaginally/intra-anally turns the device on from a sleep mode and launches a corresponding ADSAP on the user's interface device, e.g. a paired PED and/or FED. Since ideally exercises are recommended multiple times a day, such automatic operation of both the device and a corresponding application through detecting an action within a sleep mode or predetermined time of day/time period since last use etc. significantly ease the use of the ADDEV. Further, referring to FIG. 17 with a low profile self-contained ADDEV the user may receive triggers to perform exercises and perform them without explicitly activating the ADSAP etc. For example, the ADSAP may "hidden" on the user's PED user interface and provide discrete prompts and/or texts for example. During exercise sequences the user may be provided with an icon that flashes to indicate perform an exercise or may alternatively select to receive an audible prompt via wired and/or wireless connected headphones. Within other embodiments of the invention the ADSAP may be linked to a thin client version installed on a user's FED so that whilst at work they can perform the exercise discretely without requiring access to their PED.

Figure 17:
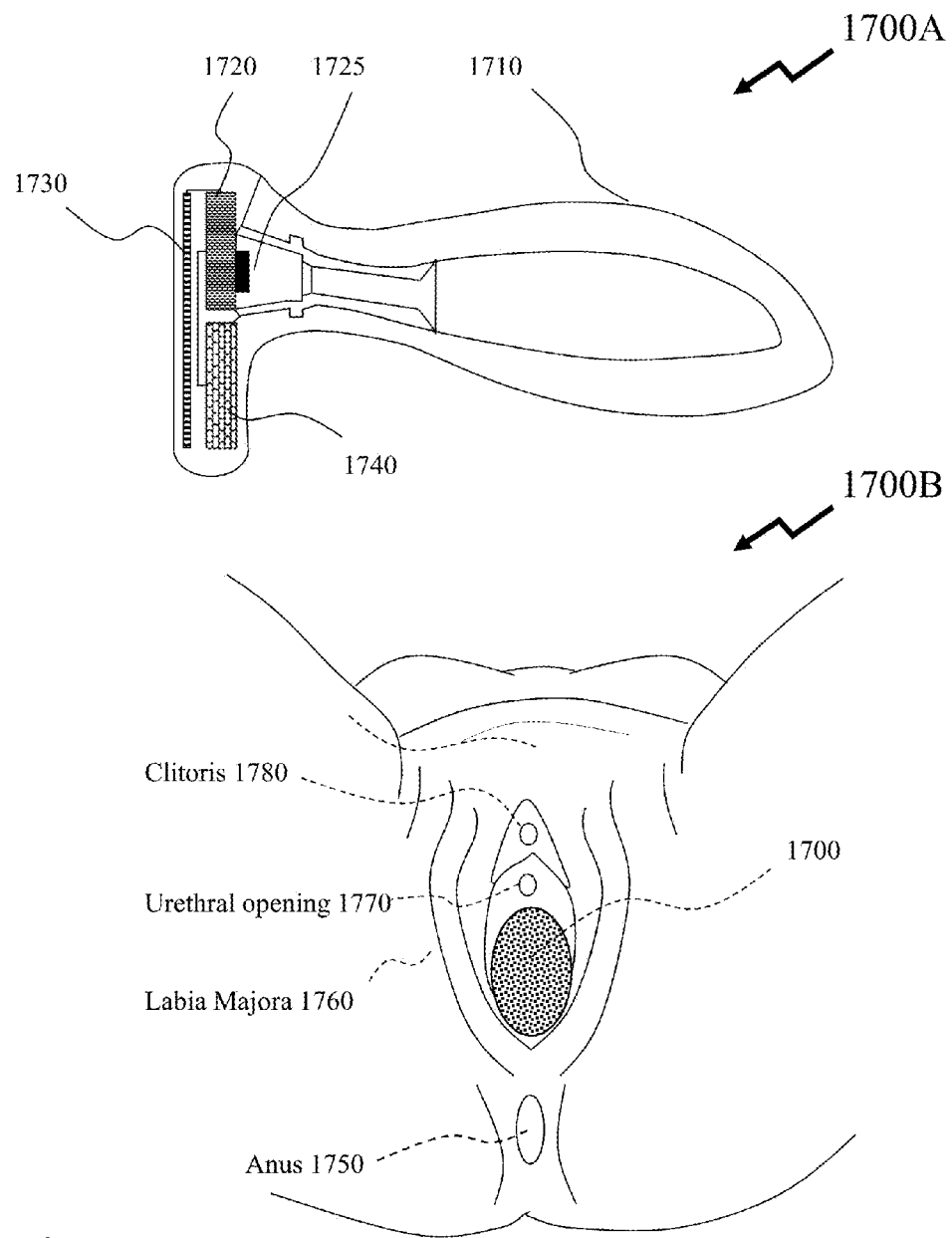
FIG. 17 depicts a side view and in use view of an adult device according to an embodiment of the invention designed for extended insertion and worn as a wearable device.

Similarly referring to FIG. 17 there are depicted first and second views 1700A and 1700B of an ADDEV according to an embodiment of the invention wherein the ADDEV supports extended use by virtue of its low profile, low power consumption, and small external geometry. As depicted in first view 1700A the device comprises a pillow 1710 connected to a low profile socket that contains pressure sensor 1725, PCB 1720, battery 1740 and antenna 1730. The device is completely self-contained and the inventors have demonstrated embodiments of the invention exploiting low profile button cell batteries, such as a 3V IEC standard 60086 compliant button with approximately 200 mAh capacity, with operation over a period of 12 months. Accordingly, as depicted in second image 1700B the ADDEV 1700 by virtue of exploiting button cells with dimensions of 20 mm diameter and 3 mm thick (0.8"×0.125") can therefore be very compact and be worn. As depicted in legs-open depiction in second image 1700B the device 1700 is depicted inserted and projecting down towards the user's anus 1750 and fitting within their labia majora 1760. Accordingly, the device 1700 leaves uncovered the user's urethral opening 1770 and clitoris 1780.

In some embodiments of the invention, the user's device measures radio signal strength from the device, such as Received Signal Strength measurements, to determine an approximate distance between the device and the user's interface device. This determined distance may then be used to change the user's interface device parameters, such as volume, type of display, or disabling of feedback entirely. In some embodiments of the invention, such distance determination may be used to initiate or encourage initiation of an exercise. For example, such initiation may be accomplished by simply placing the device next to the user's smart phone.

In some embodiments of the invention the ADDEV stores data so that the device may be used effectively and repeatedly without any communications connection. Then, later, if the ADDEV establishes communication, the stored data is then communicated from the ADDEV so as to have a complete record outside the ADDEV of exercise data and history.

Figure 18:
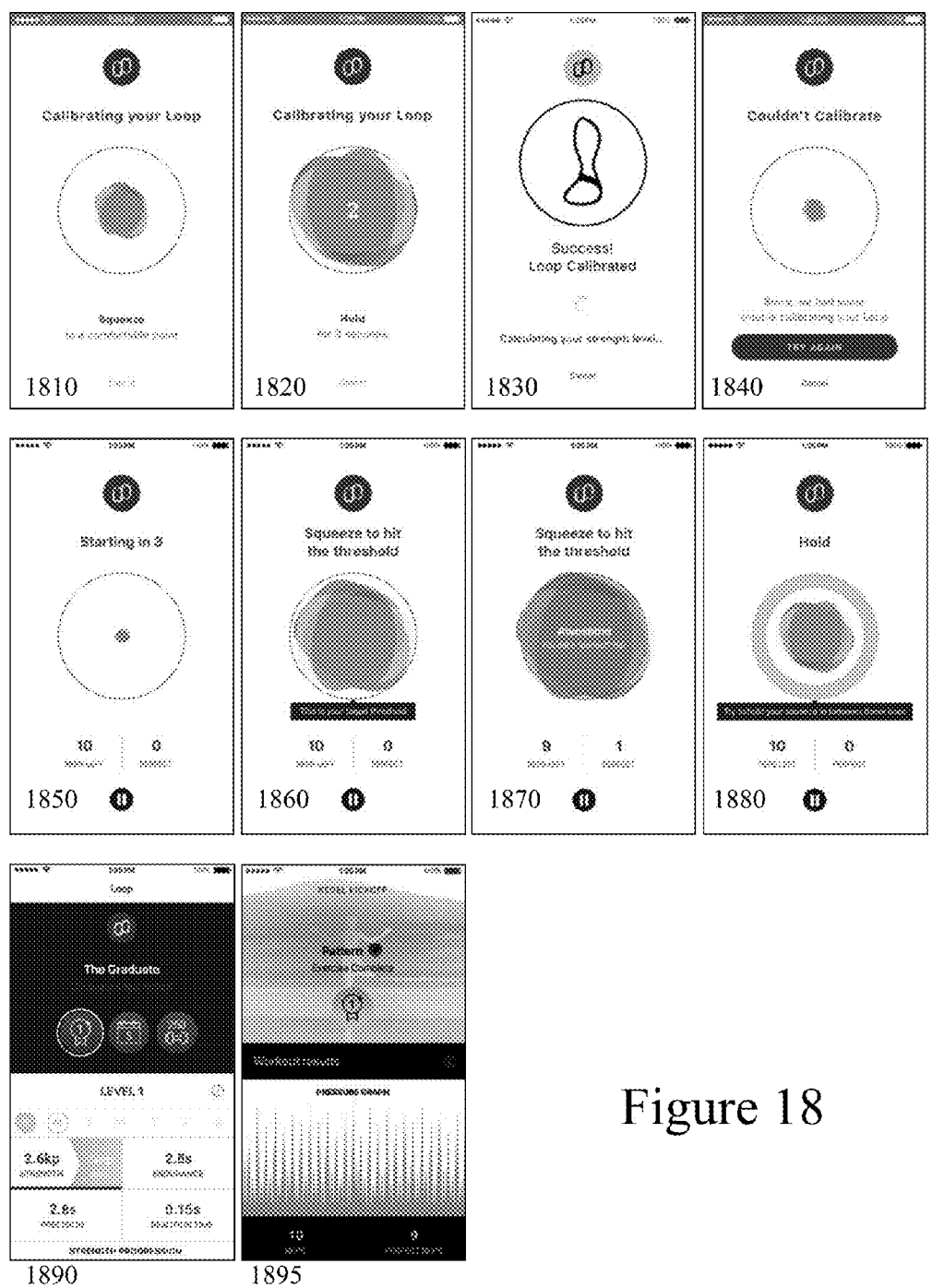
FIG. 18 depicts screenshots from an application in execution upon a portable electronic device providing a user interface for an adult device according to an embodiment of the invention.

Now referring to FIG. 18 there are depicted first to tenth screenshots of a user interface presented by a software application upon a PED (or optionally FED) such as Electronic Device 1604 in FIG. 16. Accordingly, the adult device software application (ADSoAp) allows the user to establish, for example, one or more profiles for the ADDEV, one or more profiles for themselves, and establish-monitor-track progress towards sexual wellness. However, as evident from first to fourth screens 1810 to 1840 the ADSoAp also provides the user with a calibration process for the ADDEV which may involve solely use within the intended orifice(s) or it may include actions performed by the user external to the intended orifice(s) such as an initial "at rest" calibration and a calibration wherein the user flattens the pillow with their hands or another weight to establish essentially full scale reading. Optionally, the user may be asked to pinch the device between finger and thumb, for example. Accordingly, first to fourth screens 1810 to 1840 depict:

First screen 1810 wherein the user is within a calibration routine and is asked to squeeze to a comfortable point (with the ADDEV) inserted;

Second screen 1820 wherein the user is subsequently presented with a timer relating to how long they need to squeeze;

Third careen 1830 indicating a successful calibration step completed; and

Fourth screen 1840 indicating an unsuccessful calibration step.

Subsequently in use the user is presented with a series of screens relating to potential exercises, current exercises, etc. as known within the prior art. Examples of exercise user interface screens are depicted in fifth to eighth screens 1850 to 1880 respectively, wherein:

Fifth screen 1810 wherein the user is ready to exercise and is presented with a countdown;

Sixth screen 1860 wherein the user is subsequently presented with a display for an exercise indicating their current "squeezing" against a target;

Seventh careen 1870 wherein the user is subsequently presented with a display for a successful "rep" (sequence of "squeeze" and relax) exercise indicating that they must "squeeze" within a range and hold; and Eighth screen 1880 wherein the user is presented with a display for another exercise indicating that they must "squeeze" within a range and hold.

It would be evident that the display format presented within first to eighth images 1810 to 1880 allows for concurrent display of readings derived from multiple sensors within multiple chambers and that the target may be modified to reflect where the user should focus attention and develop more control over their muscles, for example, between left/right; top/bottom and front/back. Other sensor data such as heart rate, blood pressure, blood flow, oxygenation etc. can be presented on the display with formats as known within the art. Ninth screen 1890 depicts a summary screen presented to a user with derived physical data such as an indication of strength (in kilopascal, kp, in this instance) whilst tenth screen 1895 presents temporally depicted pressure information. Optionally, the screens depicting the user's exercise may include schematics of the user's anatomy to help them visualize what they are doing and may include these in animated format such that the user receives visual indication of what they have done in addition to simply a number on a screen.

Whilst within the preceding Figures the body of the insertable portion has not been described or depicted in a large amount of detail it would be evident that portions of the ADDEVs not exploiting a compressible pillow, such as an anal vibrator, clitoral stimulator etc. may be similarly constructed and shaped as one or more prior art dildos and/or vibrators or other ADDEVs. The outer surface of the insertable portion of the ADDEV may be smooth, contoured, grooved, ribbed, and/or comprise bumps and/or nubbies. Optionally, the contours may extend further across the upper surface of the adult device or they may be more centrally limited. Optionally, the depth, spacing, and number of grooves may vary as well as their surface profile from symmetric to asymmetric etc. Optionally, the upper surface may be smooth or it may be profiled by the distribution of nubbies across upper surface regions in some embodiments of the invention. Within others features that have multiple "fingers" or "fronds" may be employed to provide different sensations. Optionally different regions of the ADDEV may have different structures such as nubbies, grooves, smooth areas etc. on the upper central bump as well as its sides.

The adult device may be provided in a range of physical sizes overall exploiting the relative dimensions and radii etc. described supra in respect of FIGS. 1 to 4 such that, for example, the length of the inserted vaginal portion may be 50 mm, 75 mm, 100 mm, 125 mm, 150 mm, or 200 mm for example (3", 4", 5", 6" or 8") and it's lateral dimensions may be, for example, 15 mm, 25 mm, 35 mm, 40 mm, 50 mm, or 75 mm (0.6", 1", 1.4", 1.6", 2", or 3"). Where an anal insertion element is provided its length and lateral dimensions may be over a similar range as the vaginally inserted portion. Whilst typically the vaginally inserted portion will have limited width variations along its length an anally inserted portion may have larger width variations and may have a length/width ratio lower than the vaginally inserted portion. However, other dimensions, aspect ratios, cross-section geometries etc. may be employed without departing from the scope of the invention.

Typically, the construction of an ADDEV such as depicted within embodiments of the invention described in respect of FIGS. 1 to 17 will employ a central scaffold which provides rigidity to the ADDEV in those regions requiring it which may be surrounded by a shell and then a casing. Whilst the casing and shell may be transparent or semi-transparent over portions or all of the ADDEV it is common for the ADDEV to be opaque. Within those regions of the ADDEV that are flexible, such as the pillow, for example, the structure may have no scaffold or it may employ a scaffold that has properties commensurate with that portion of the ADDEV. For example, within the pillow for providing dividing sections between chambers the scaffold may be formed from an elastic material on a frame embedded within the pillow walls such that the dividing section maintains its profile as the pillow expands and contracts. The pillow may be formed in multiple steps according to its profile, thickness, etc.

An outer casing may be coloured based upon skin colour tones based upon ethnicity or personal preference, e.g. Caucasian, Negroid, Mongol, light, dark, etc. as well as single colour, binary colour, multiple colour etc. According to the complexity acceptable then the outer casing may be formed from a variety of colours and/or be patterned for a specific design. Typically, such colours will be part of a silicone or other elastomer employed in forming the casing although in other embodiments of the invention the casing may be coloured once formed and a protective fluid proof, non-toxic, non-abrasive coating formed atop these applied colours. Such instances of applied colours may include metallic lacquers, particulate lacquers for "sparkle", etc. Optionally, the silicone may be clear and either embedded into the silicone or a shell of the adult device are LEDs, such as multi-colour LEDs for example, allowing the colour of the adult device to be varied either statically or dynamically, such as for example in response to commands from an associated PED generated in response to controlling ambient light, music, audiovisual content etc. Beneficially, medical grade silicone is clear thereby removing the requirement for any additional coating (e.g. food grade urethane) in conjunction with pigmented silicones. Accordingly, an adult device may with medical grade silicone be clear and formed from an initial sticky soft silicone, e.g. 20 durometer, with a micro-layer (spray coated for example) of high durometer medical grade silicone, for example 70-90 durometer, to create "slippery" surface and avoid silky smooth surface that typically requires use of urethane coating.

Typically, the casing for the ADDEV will be formed from a non-toxic, hypoallergenic silicone to provide a safe smooth surface although some regions of the ADDEV may be coated, textured and/or finished with a variation from that of the remainder of the casing in order to enhance or promote retention of the ADDEV against the user's skin or clothing. Typically, the outer surface of the casing will be formed to provide low friction as well as resistance to lubricants that may or may not be employed. According to the casing material and sealing of the device then it may be cleaned or sterilized to a medical standard, for example through a domestic dishwasher cycle. Alternatively, the device may be chemically cleaned or sterilized to a medical standard.

Typically, within the outer silicone or elastomeric casing is a shell that houses internally, in the embodiments presented, vibratory motors, battery, control circuit, pressure sensor, sensors, and charging port. Within embodiments of the invention other functional elements may be employed for generating physical stimulus, providing user interface, wireless transceiver for communicating to an associated electronic device (PED or FED) or other ADDEV, etc. Within the description of embodiments of the invention and associated figures such elements are not presented for clarity of description, figures etc. However, as described at the end of the specification such elements may or may not be implemented within embodiments of the invention. Accordingly, the shell may comprise a single chamber or a plurality of chambers and may be formed from one piece part or multiple piece parts which are connected via the casing and/or discrete or connected by a central portion with different degrees of rigidity range from solid to a living hinge.

Optionally, the ADDEV may employ one, two, three or more motors as well as actuators of one, two or more different technical approaches. For example one or more vibratory motors may provide high end vibrations whilst one or more vibratory or high impact gear-reduced motors may provide a low frequency "rumble" from larger weighted motors or through controlled frequency offset "throbbing." Optionally, linear vibratory motors may be disposed within the regions on the outer surface of the recipient's body or the inserted portion(s) whilst generally rotating asymmetric weight motors are within the shell of the inserted portion(s). Optionally, the outer surface of the ADDEV may provide electrical stimulation contacts through metal contacts or conductive silicone pads for example at predetermined locations on the inserted portion as well as the discussion supra in respect the clitoral region. Equally, contacts may be disposed on the lower outer portion of the ADDEV to engage the recipient's lower labial lips, etc.

Embodiments of the invention with respect to controlling an ADDEV such as described within the embodiments of the invention supra in respect of FIGS. 1 to 17 may employ one or more methodologies as known within the art. Such control may be provided, for example, through a remote control wirelessly connected to the ADDEV, a PED or FED wirelessly connected to the ADDEV, a remote control wired to the ADDEV, and a control interface on the ADDEV allowing selection of predetermined program. In instances of wireless interfaced controllers the control may be local, i.e. by a user engaged in a sexual activity involving the ADDEV, or the control may be remote.

Embodiments of the invention with respect to powering an ADDEV such as described within the embodiments of the invention supra in respect of FIGS. 1 to 17 may employ one or more methodologies as known within the art. For example, the ADDEV may comprise a rechargeable battery or batteries within the shell which may be of a standard form/type, such as AA, AAA, etc. or custom to the ADDEV and/or another product. Alternatively, the ADDEV may employ non-rechargeable batteries and require an access to allow in insertion/removal of the battery or batteries or the ADDEV may be disposed of once the batteries have been exhausted. Optionally, the ADDEV may be powered directly from electrical mains supply through a transformer to support extended use or high power requirements not supportable by realistic battery configurations. Where an electrical connection is made to the ADDEV this may be similarly via a technique known in the prior art such as plug-socket connection, magnetic electrical connectors, etc.

Whilst the ADDEV has been primarily described with respect to an ADDEV for use in providing stimulation to a female user vaginally whilst a user orally stimulated their clitoris and/or clitoral region it would be evident that embodiments of the invention may also be employed providing stimulation of the external vaginal area, labia, perineum etc. as well as male perineum, testes, etc.

Embodiments of the invention with respect to the ADDEV such as described within the embodiments of the invention supra in respect of FIGS. 1 to 17 may employ a "sticky" surface for the outer surface engaging a recipient's body (e.g. being formed from a low durometer silicone for example) so that the surface is designed to "stick" to skin so it stays in place. This "sticky" surface may be mirror surface, matt or textured for grip. Examples of materials may be those with durometer ideal Shore A10 or lower, Shore A5 or lower, or Shore A1. In some embodiments of the invention a region or regions of the casing may be formed from a gel such as the Ecoflex™ platinum catalyzed silicones for example certified to ISI 10993-10 for skin irritation/sensitization and having, for example, Shore 00-50 hardness (below the Shore A scale), Shore 00-30 hardness, Shore 00-20 hardness, or Shore 00-10 hardness. Within embodiments of the invention the footprint of the casing may be significantly larger than the shell (mechanical assembly) footprint, larger than the shell print, approximately the same as the shell footprint, and smaller than the shell footprint. Where the shell footprint is larger than the shell footprint its mechanical structure may be such that it does not droop under its weight/gravity when held free, droops a small amount, droops a moderate amount, or droops completely according to the desired characteristics. In embodiments of the invention the casing around the shell may act like a thin sheet (<<1 mm thick), like a fabric or material, like a sheet (~1 mm), a thick sheet (>1 mm). Optionally, the lower surface of the casing designed for placement against a user's groin/stomach may be sticky and when washed recover this stickiness in its entirety or in different regions or areas.

Optionally, the outer surface which may contact the user providing oral stimulation may be smooth with low friction to human skin, smooth with minimal friction to human skin, smooth with moderate friction to human skin, smooth with high friction to human skin in its entirety or in different regions or areas. Alternatively, the surface may be smooth, textured, and/or rough and have low friction, negligible friction, moderate friction, and/or high friction in its entirety or in different regions or areas. Optionally, the surface may be textured with low friction to human skin, textured with minimal friction to human skin, textured with moderate friction to human skin, or textured with high friction to human skin in its entirety or in different regions. Optionally, the surface of the casing in its entirety or in different regions or areas may be used in conjunction with disposable sheets that provide adhesion and/or friction in predetermined levels.

Within embodiments of the invention the casing, for example formed from silicone, is the only material surrounding the casing and the surface profile is derived from applying the casing to the contoured surface of the shell. In other embodiments of the invention the surface profile is derived from multiple applications of a single material forming the casing. In other embodiments of the invention an additional material or materials are disposed between the shell and the casing. This, may for example, be a preform formed from the same material as the casing such that the casing is applied as a single or multiple dip coating for example, a preform formed from another silicone of different characteristics to the casing, a preform formed from a plastic, a preform formed from a low density foam, from a medium density foam, or a high density foam. Alternatively, a combination of materials may be employed such as two or more plastics, two or more foams, a foam and a plastic, a foam and a silicone, a form and metal. The materials may be layered, inserted, embedded, etc. without departing from the scope of the invention. However, a characteristic of these materials is the transmission of vibratory motion arising from the active elements within the ADDEV according to embodiments of the invention. Within passive embodiments this characteristic of material selection is removed.

Within the embodiments of the invention with active elements these are mounted to predetermined portions of the shell which is surrounded by the casing. Other embodiments may exploit a passive inserted portion mimicking a dildo function rather than a vibrator. As noted above the ADDEV according to embodiments of the invention may, in addition, to a silicone outer comprise one or more materials to provide mechanical structures such as ridges, shell, scaffold, etc. whilst the casing is smooth.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A sexual wellness device comprising:
    a pillow formed from a flexible material defining an inner volume and having an opening at an end;
    a socket formed from an inflexible material having in a first predetermined location a fitting onto which the open end of the pillow mounts, a pressure sensor fluidically coupled to the fitting, a controller electrically coupled to the pressure sensor, and a battery electrically connected to at least the controller, and
    at least one of:
        a second pillow attached to the socket for insertion into an anus of a user when the pillow is inserted into the vagina;
        a clitoral stimulator attached to the socket;
        an anal element attached to the socket; and
        a third pillow for demountably replacing the pillow.

2. The sexual wellness device according to claim 1, wherein
    the geometry of the pillow is defined by a central axial line which is the sagittal plane of a female user of the sexual wellness device and is aligned to the superior-inferior axis of female user's vagina when inserted.

3. The sexual wellness device according to claim 1, wherein
    the geometry of the pillow is defined by the following:
    a tip towards the superior of the superior-inferior axis of the female user's vagina;
    an upper surface facing an anterior surface of the vagina with left and right portions of the upper surface being different profiles wherein the left and right portions are defined relative to a first plane vertically defined at a first predetermined lateral offset to a longitudinal axis of the sexual wellness device; and
    a lower surface facing a posterior surface of the vagina with left and right portions of the lower surface being different profiles wherein the left and right portions are defined relative to a second plane vertically defined at a second predetermined lateral offset to the longitudinal axis of the sexual wellness device.

4. The sexual wellness device according to claim 1, wherein
the socket has an external profile allowing the device to be gripped in a first configuration and a second configuration, and wherein:
in the first configuration, the sexual wellness device is gripped by a user of the sexual wellness device on a first surface and a second surface of the sexual wellness device where these are disposed at different locations along a longitudinal axis of the sexual wellness device; and
in the second configuration, the sexual wellness device is gripped by a user for insertion into an orifice of another user on a third surface and a fourth surface of the sexual wellness device where these are disposed at different locations parallel to an offset from the longitudinal axis of the sexual wellness device.

5. The sexual wellness device according to claim 1, wherein
the inner volume of the pillow is divided into a plurality of chambers and each chamber is coupled to a pressure sensor.

6. The sexual wellness device according to claim 1, wherein,
disposed within at least one of the pillow and the socket, is at least one of a photoplethysmography (PPG) sensor and a laser Doppler imaging (LDI) sensor, and wherein
the at least one of the PPG sensor and the LDI sensor comprise an optical emitter of predetermined first characteristics and an optical detector of predetermined second characteristics.

7. The sexual wellness device according to claim 1, wherein,
disposed within at least one of pillow and the socket, is at least one microphone of a plurality of microphones.

8. The sexual wellness device according to claim 1, wherein,
disposed within at least one of pillow and the socket, is at least one temperature dependent resistive element of a plurality of temperature dependent resistive elements.

9. The sexual wellness device according to claim 1, wherein,
disposed within at least one of pillow and the socket, is at least one electrical contact of a plurality of electrical contacts, each electrical contact for at least one of the application to and the measurement of an electrical signal.

10. A method of adjusting sexual wellness for a user comprising:
providing a pillow formed from a flexible material defining an inner volume and having an opening at an end;
providing a socket formed from an inflexible material having in a first predetermined location a fitting onto which the open end of the pillow mounts, a pressure sensor fluidically coupled to the fitting, a controller electrically coupled to the pressure sensor, and a battery electrically connected to at least the controller;
providing at least one of:
a second pillow attached to the socket for insertion into an anus of a user when the pillow is inserted into the vagina;
a clitoral stimulator attached to the socket;
an anal element attached to the socket; and
a third pillow for demountably replacing the pillow; and
monitoring an action of the user with respect to the pillow resulting in a pressure fluctuation and providing the user with feedback as to their performance.

11. The method of providing a sexual wellness device for a user according to claim 10, wherein
the geometry of the pillow is defined by a central axial line which is the sagittal plane of a female user of the sexual wellness device and is aligned to the superior-inferior axis of female user's vagina when inserted.

12. The method of providing a sexual wellness device for a user according to claim 10, wherein
the geometry of the pillow is defined by the following:
a tip towards the superior of the superior-inferior axis of the female user's vagina;
an upper surface facing an anterior surface of the vagina with left and right portions of the upper surface being different profiles wherein the left and right portions are defined relative to a first plane vertically defined at a first predetermined lateral offset to a longitudinal axis of the sexual wellness device; and
a lower surface facing a posterior surface of the vagina with left and right portions of the lower surface being different profiles wherein the left and right portions are defined relative to a second plane vertically defined at a second predetermined lateral offset to the longitudinal axis of the sexual wellness device.

13. The method of providing a sexual wellness device for a user according to claim 10, wherein
the socket has an external profile allowing the device to be gripped in a first configuration and a second configuration, and wherein
in the first configuration, the sexual wellness device is gripped by a user of the sexual wellness device on a first surface and a second surface of the sexual wellness device where these are disposed at different locations along a longitudinal axis of the sexual wellness device; and
in the second configuration, the sexual wellness device is gripped by a user for insertion into an orifice of another user on a third surface and a fourth surface of the sexual wellness device where these are disposed at different locations parallel to an offset from the longitudinal axis of the sexual wellness device.

14. The method of providing a sexual wellness device for a user according to claim 10, wherein
the inner volume of the pillow is divided into a plurality of chambers and each chamber is coupled to a pressure sensor.

15. The method of providing a sexual wellness device for a user according to claim 10, wherein,
disposed within at least one of the pillow and the socket, is at least one of a photoplethysmography (PPG) sensor and a laser Doppler imaging (LDI) sensor, and wherein
the at least one of the PPG sensor and the LDI sensor comprise an optical emitter of predetermined first characteristics and an optical detector of predetermined second characteristics.

16. The method of providing a sexual wellness device for a user according to claim 10, wherein,
disposed within at least one of pillow and the socket, is at least one microphone of a plurality of microphones.

17. The method of providing a sexual wellness device for a user according to claim 10, wherein, disposed within at least one of pillow and the socket, is at least one temperature dependent resistive element of a plurality of temperature dependent resistive elements.

18. The method of providing a sexual wellness device for a user according to claim 10, wherein,
disposed within at least one of pillow and the socket, is at least one electrical contact of a plurality of electrical contacts, each electrical contact for at least one of the application to and the measurement of an electrical signal.

* * * * *